United States Patent
Nicolai et al.

(10) Patent No.: US 6,180,651 B1
(45) Date of Patent: *Jan. 30, 2001

(54) DIARYLMETHYLIDENEFURAN DERIVATIVES, PROCESSES FOR THEIR PREPARATION AND THEIR USES IN THERAPEUTICS

(75) Inventors: Eric Nicolai, Rueil Malmaison; Jean-Marie Teulon, La Celle Saint Cloud, both of (FR)

(73) Assignee: Bristol-Myers Squibb, Princeton, NJ (US)

(*) Notice: Under 35 U.S.C. 154(b), the term of this patent shall be extended for 0 days.

This patent is subject to a terminal disclaimer.

(21) Appl. No.: 09/150,388

(22) Filed: Sep. 9, 1998

Related U.S. Application Data

(63) Continuation-in-part of application No. 09/125,846, filed on Aug. 26, 1998, now abandoned, which is a continuation-in-part of application No. 08/825,242, filed on Mar. 27, 1997, now Pat. No. 5,807,873, which is a continuation-in-part of application No. 08/714,742, filed on Sep. 16, 1996, now abandoned.

(30) Foreign Application Priority Data

Apr. 4, 1996 (FR) .................................. 96 04326
Jun. 26, 1996 (FR) .................................. 96 07922

(51) Int. Cl.⁷ ...................... C07D 405/06; A61K 51/44
(52) U.S. Cl. .................. 514/336; 514/473; 546/284.4; 549/323; 549/472
(58) Field of Search ............... 546/284.4, 256; 549/323, 60; 514/336, 473

(56) References Cited

U.S. PATENT DOCUMENTS

| | | | |
|---|---|---|---|
| 5,010,102 | 4/1991 | Felman et al. | 514/473 |
| 5,134,128 | 7/1992 | Lee et al. | 514/63 |
| 5,202,350 | 4/1993 | Zusi et al. | 514/461 |
| 5,259,701 | 11/1993 | Gerhart et al. | 405/216 |
| 5,387,606 | 2/1995 | Garst | 514/461 |
| 5,389,673 | 2/1995 | Felman et al. | 514/473 |
| 5,541,221 | 7/1996 | Garst | 514/461 |

FOREIGN PATENT DOCUMENTS

| | | |
|---|---|---|
| WO94/15932 | 7/1994 | (WO) . |
| WO95/00501 | 1/1995 | (WO) . |
| WO96/08482 | 3/1996 | (WO) . |
| WO96/36623 | 11/1996 | (WO) . |
| WO98/43966 | 10/1998 | (WO) . |

OTHER PUBLICATIONS

Gilbert, et al., *J. Med. Chem.*, 1983, 26: 693–699.
Katsumi, et al., *Chem. Pharm. Bull.*, 1986, 34(1): 121–129.
Katsumi, et al., *Chem. Pharm. Bull.*, 1986, 34(4): 1619–1627.

Primary Examiner—Jane Fan

(57) ABSTRACT

The present invention relates to derivatives of the formula

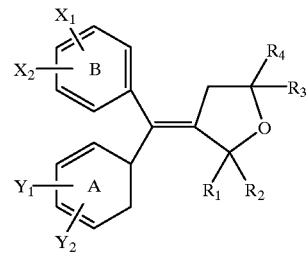

the process for their preparation, and to their uses in therapeutics, especially as drugs with anti-inflammatory, analgesic and chemopreventive properties.

17 Claims, No Drawings

DIARYLMETHYLIDENEFURAN DERIVATIVES, PROCESSES FOR THEIR PREPARATION AND THEIR USES IN THERAPEUTICS

This is a continuation-in-part of U.S. application Ser. No. 09/125,846, filed Aug. 26, 1998, now abandoned which is a continuation-in-part of U.S. application Ser. No. 08/825,242, filed Mar. 27, 1997, now U.S. Pat. No. 5,807,873 which is a continuation-in-part of U.S. application Ser. No. 08/714,742, filed Sep. 16, 1996, now abandoned, claiming priorities from French Patent Application No. 9604236, filed on Apr. 4, 1996 and from French Patent Application No. 9607922, filed on Jun. 26, 1996.

The present invention relates, by way of novel products, to the diarylmethylidenefuran derivatives of general formula (I).

One of the biotransformation pathways of arachidonic acid is the cyclooxygenase pathway, which makes it possible to transform arachidonic acid to PGG2 and then PGH2. Recent work on the cloning and sequencing of cyclooxygenase has demonstrated the presence of two is enzymes, COX-1 and COX-2, in several species and particularly in man. The first is a constitutive enzyme which is expressed in the majority of tissues, while the second, which is expressed in a few tissues such as the brain, is inducible in the majority of tissues by numerous products, in particular by the cytokines and the mediators produced during the inflammatory reaction. Each enzyme has a different role and the inhibition of COX-1 or COX-2 will not have identical consequences. The inhibition of COX-1 will cause a decrease in the prostaglandins participating in homeostasis, which can give rise to side effects. The inhibition of COX-2 will cause a decrease in the prostaglandins produced in an inflammatory situation. Thus the selective inhibition of COX-2 makes it possible to obtain a well-tolerated anti-inflammatory.

The compounds of the invention make it possible to achieve this selective inhibition. The compounds in question consequently have a very valuable pharmacological profile insofar as they possess anti-inflammatory and analgesic properties while being remarkably well tolerated, especially at the gastric level. They will be particularly indicated for the treatment of inflammatory phenomena and for the treatment of pain.

An example of their use which may be mentioned is the treatment of arthritis, especially rheumatoid arthritis, spondylitis, gouty arthritis, osteoarthritis and juvenile arthritis, autoimmune diseases and lupus erythematosus. They will also be indicated for the treatment of bronchial asthma, dysmenorrhea, tendinitis, bursitis and dermatological inflammations such as psoriasis, eczema, burns and dermatitis. They can also be used for the treatment of gastrointestinal inflammations, Crohn's disease, gastritis and ulcerative colitis, in the prevention of cancer, especially adenocarcinoma of the colon, in the prevention of neurodegenerative diseases, particularly Alzheimer's disease, in the prevention of stroke and epilepsy, and in the prevention of premature labour.

Their analgesic properties also enable them to be used for any painful symptoms, especially in the treatment of myalgia, articular pain or neuralgia, dental pain, herpes zoster and migraine, in the treatment of rheumatic complaints and pain of cancerous origin, and also as complementary treatments for infectious and febrile states.

The present invention further relates to the process for the preparation of said products and to their applications in therapeutics.

Certain derivatives are described in the literature as having selective cyclooxygenase-2 inhibiting properties. The compounds described in the following patent applications may be cited:
WO 95 00501 A (Merck Frosst Canada Inc.)
WO 94 15932 A (G. D. Searle and Co.)
WO 96 08482 A (Merck and Co. Inc.)

Generally, the majority of the compounds, described in these documents as selective cyclooxygenase-2 inhibitors, are 5-membered heterocyclic derivatives substituted with two aromatic rings which are bound directly onto the heterocycle and which are on two carbon atoms adjacent to this heterocycle.

The applicant has discovered in a surprising way that the derivatives bearing the two aromatic rings on a same carbon (these two aromatic rings being linked to the heterocycle not directly but by an intermediate double bond), have remarkable selective cyclooxygenase-2 inhibiting properties.

These diarylmethylidene furan derivatives are characterised in that they have the general formula (I):

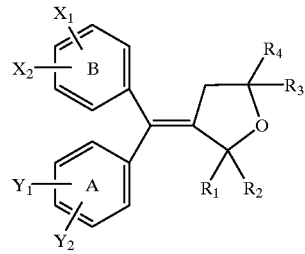

Formula (I)

in which:
the rings A and B independently are:
a phenyl radical,
a naphthyl radical,
a radical derived from a heterocycle comprising 5 to 6 members and possessing from 1 to 4 heteroatoms, or
a radical derived from a saturated hydrocarbon ring having from 3 to 7 carbon atoms;
at least one of the substituents $X_1$, $X_2$, $Y_1$ or $Y_2$ is necessarily:
an —$S(O)_n$—R group, in which n is an integer equal to 0, 1 or 2 and R is a lower alkyl radical having 1 to 6 carbon atoms or a lower haloalkyl radical having 1 to 6 carbon atoms, or
an —$SO_2NH_2$ group;
and is located in the para position,
the others independently being independently:
a hydrogen atom,
a halogen atom,
a lower alkyl radical having 1 to 6 carbon atoms,
a trifluoromethyl radical, or
a lower O-alkyl radical having 1 to 6 carbon atoms,
or even
$X_1$ and $X_2$ or $Y_1$ and $Y_2$ are a methylenedioxy group; and
$R_1$, $R_2$, $R_3$ and $R_4$ independently are:
a hydrogen atom,
a halogen atom,
a lower alkyl radical having 1 to 6 carbon atoms,
a lower haloalkyl radical having 1 to 6 carbon atoms, or an aromatic radical selected from the group consisting of phenyl, naphthyl, thienyl, furyl and pyridyl;

or even $R_1R_2$ or $R_3R_4$ are an oxygen atom, or even $R_1,R_2$ or $R_3,R_4$, together with the carbon atom to which they are attached, form a saturated hydrocarbon ring having from 3 to 7 carbon atoms.

In the description and the claims, lower alkyl is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

Lower haloalkyl radical is understood as meaning an alkyl radical having 1 to 6 carbon atoms in which 1 to 7 hydrogen atoms have been substituted by 1 to 7 halogen atoms. A lower haloalkyl radical is for example a trifluoromethyl radical, a 2,2,2-trifluoroethyl radical, a pentafluoroethyl radical, a 2,2-difluoro-3,3,3-trifluoropropyl radical, a heptafluoropropyl radical or a chloromethyl or bromomethyl radical.

Halogen is understood as meaning a chlorine, bromine, iodine or fluorine atom.

Saturated hydrocarbon ring having from 3 to 7 carbon atoms is understood as meaning cyclopropane, cyclobutane, cyclopentane, cyclohexane or cycloheptane.

Radical derived from a heterocycle means any aromatic ring containing from one to four heteroatoms in its ring: nitrogen, oxygen or sulphur.

Amongst these rings, pyridine, furan, thiophen, as well as pyrrole, imidazole, pyrazole, pyrazine, pyrimidine, pyridazine, oxazole, oxadiazole, thiazole and thiadiazole are particularly preferred.

The above-mentioned derivatives of formula (I) can have asymmetric centres and/or can exist in the form of cis or trans derivatives. The invention covers the racemates and the mixtures of cis and trans compounds, but also covers the optically active products, the cis derivatives and the trans derivatives taken independently. These pure products will be obtained by the methods known to those skilled in the art, in particular by chromatography, especially on chiral columns in the case of optical isomers. This separation may also be carried out in certain cases by simple recrystallisation. The separation may be carried out either on the final product or on an intermediate of the synthesis, in this case, the rest of the synthesis will respect the stereochemistry of the intermediate molecule.

Advantageously the derivatives according to the invention are the derivatives of formula (I) above in which:

the rings A and B independently are:
a phenyl,
naphthyl,
pyridyl,
furyl, or
thienyl, at least one of the substituents $X_1$, $X_2$, $Y_1$ or $Y_2$ is necessarily an $SCH_3$, $SO_2CH_3$ or $SO_2NH_2$ group,
the others independently being:
a hydrogen atom,
a halogen atom,
a lower alkyl radical having 1 to 6 carbon atoms,
a trifluoromethyl radical, or
a lower O-alkyl radical of 1 to 6 carbon atoms;

$R_1R_2$ are an oxygen atom; and $R_3,R_4$ independently are a hydrogen atom or a lower alkyl radical having 1 to 6 carbon atoms.

Within the framework of the present invention, it will be advantageous to use a compound of formula (I) in which at least one of the following conditions is satisfied:

the ring B is a phenyl radical, $X_1$ is a 4-$SO_2CH_3$ group or a 4-$SO_2NH_2$ group, $X_2$, is a hydrogen atom, the ring A is a phenyl radical or a pyridyl radical, $Y_1$ is a fluorine atom, a chlorine atom a bromine atom or a methyl radical, $Y_2$ is a hydrogen atom, a fluorine atom or a chlorine atom, $R_1R_2$ are an oxygen atom, $R_3$ is a hydrogen atom, and $R_4$ is a hydrogen atom.

The particularly preferred compounds of the invention are the derivatives of the following formulae:

(E)-3-[1-(4-fluorophenyl)-1-(4-methanesulphonylphenyl) methylidene]dihydrofuran-2-one

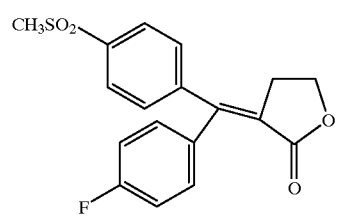

(Z)-3-[1-(4-chlorophenyl)-1-(4-methanesulphonylphenyl) methylidene]dihydrofuran-2-one

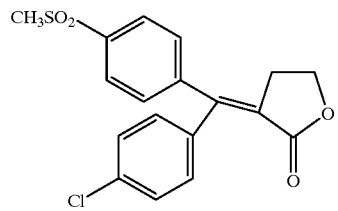

(Z)-3-[1-(3,4-dichlorophenyl)-1-(4-methanesulphonylphenyl)methylidene]-dihydrofuran-2-one

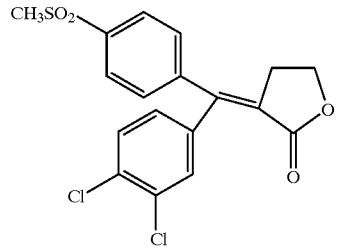

(Z)-3-[1-(6-chloropyridin-3-yl)-1-(4-methanesulphonylphenyl)methylidene]-dihydrofuran-2-one

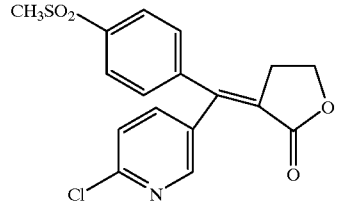

(Z)-4-[(4-chlorophenyl)-(2-oxodihydrofuran-3-ylidene)methyl]benzene sulphonamide

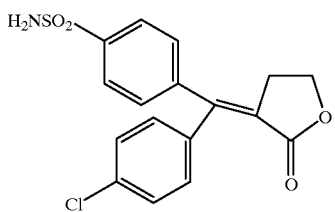

(Z)-4-[(3-fluoro-4-methylphenyl)-(2-oxodihydrofuran-3-ylidene)methyl]-benzenesulphonamide

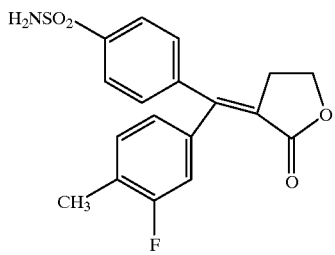

According to the invention, the compounds of formula (I) can be synthesised in the following manner:

(E)-4-[(4-fluorophenyl)-(2-oxo-dihydrofuran-3-ylidene)methyl]benzensulfonamide

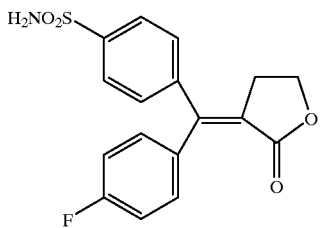

(E)-4-[(4-methylphenyl)(tetrahydro-2-oxo-3-furanylidene)methyl]benzenesulfonamide

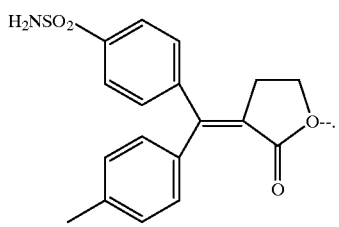

A Friedel-Crafts reaction of the acid chloride of formula (II):

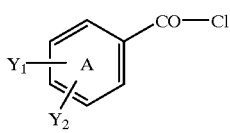

in which A, $Y_1$ and $Y_2$ are as defined above, with thioanisole will give the ketone of formula (III):

Formula (III)

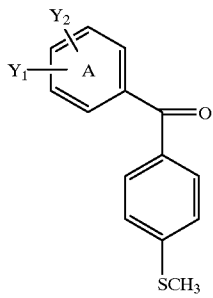

in which A, $Y_1$ and $Y_2$ are as defined above.

This ketone may also be obtained by a Grignard reaction: a reaction of a bromoaromatic magnesium derivative, which may be substituted, with p-ethylthiobenzonitrile.

Treatment of this benzophenone with an oxidising agent, for example metachloroperbenzoic acid, sodium perborate or hydrogen peroxide in the presence of a catalytic amount of molybdenum salts, will give the derivative of formula (IV):

Formula (IV)

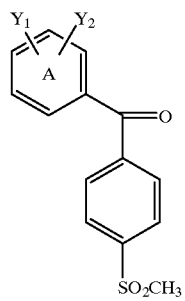

in which A, $Y_1$ and $Y_2$ are as defined above.

Treatment of the derivative of formula (IV), by a modified Reformatsky reaction with a bromobutyrolactone of formula (V):

Formula (V)

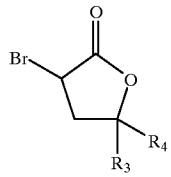

in which $R_3$ and $R_4$ are as defined above, in the presence of magnesium and a small amount of methyl iodide to initiate the reaction, will give the derivatives of formula (VI):

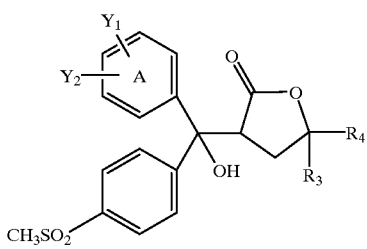

Formula (VI)

in which A, $Y_1$, $Y_2$, $R_3$ and $R_4$ are as defined above.

Finally, dehydration of the derivatives of formula (VI) by heating in toluene, for example in the presence of paratoluenesulphonic acid, or by treatment with trifluoroacetic anhydride in trifluoroacetic acid, will give the compounds of formula (I):

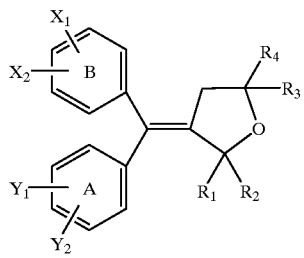

Formula (I)

in which B is a phenyl ring, $X_1$ is a 4-$SO_2CH_3$ group, $X_2$ is a hydrogen atom, $R_1R_2$ are an oxygen atom and A, $Y_1$, $Y_2$, $R_3$ and $R_4$ are as defined above.

One preparative variant consists in treating the product of formula (III) either with the derivative of formula (V) by an identical method involving a modified Reformatsky reaction, in the presence of magnesium and methyl iodide to initiate the reaction, or with lactones of formula (V'):

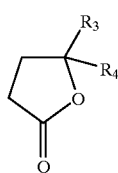

Formula (V')

in which $R_3$ and $R_4$ are as defined above, in the presence of N,N-diethylaminomagnesium bromide, prepared by reacting N,N-diethylamine with ethylmagnesium bromide, according to the reference: K. Sisido, H. Nozaki, O. Kurihara, *J. Am. Chem. Soc.*, 74, 6254 (1952), to give either the already dehydrated compounds of formula (I) or the compounds of formula (VI'):

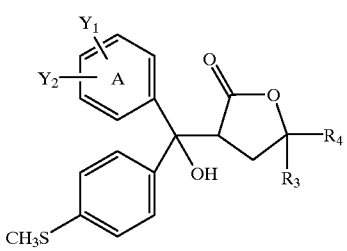

Formula (VI')

in which A, $Y_1$, $Y_2$, $R_3$ and $R_4$ are as defined above.

The compounds of formula (VI') will then be dehydrated by treatment with trifluoroacetic anhydride and trifluoroacetic acid to give the compounds of formula (I) below:

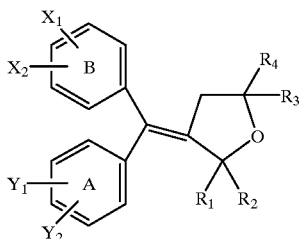

Formula (I)

in which B is a phenyl ring, $X_1$ is a 4-$SCH_3$ group, $X_2$ is a hydrogen atom, $R_1R_2$ are an oxygen atom and A, $Y_1$, $Y_2$, $R_3$ and $R_4$ are as defined above.

Treatment of the compound obtained according to this variant with metachloroperbenzoic acid or with another oxidising agent like $NaBO_3.4\ H_2O$ will give, depending on the amount of oxidising agent used, the compounds of formula (I):

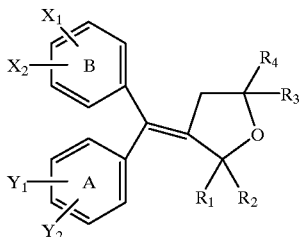

Formula (I)

in which B is a phenyl ring, $X_1$ is a 4-$SOCH_3$ group for one equivalent of oxidising agent or a 4-$SO_2CH_3$ group for two equivalents of oxidising agent, $X_2$ is a hydrogen atom, $R_1R_2$ are an oxygen atom and A, $Y_1$, $Y_2$, $R_3$ and $R_4$ are as defined above.

Another preparative variant for some compounds of formula (I) consists in treating a ketone of formula (III) with ethyl succinate, by the Stobbe reaction, in tert-butanol in the presence of sodium or potassium tert-butoxide, to give the compounds of formula (VII):

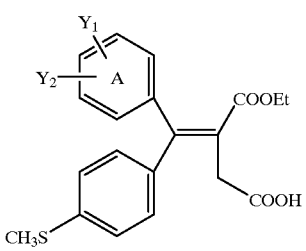

Formula (VII)

in which A, $Y_1$ and $Y_2$ are as defined above.

Selective reduction of the ester group, for example with calcium borohydride, obtained in situ from potassium borohydride and calcium chloride in ethanol, or with sodium diethyl dihydroaluminate in diethyl ether, will give, after lactonisation of the hydroxy acids obtained, the derivatives of formula (VIII):

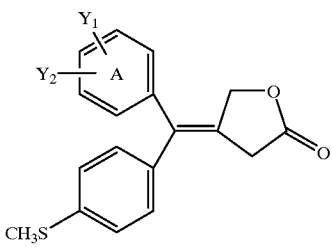

Formula (VIII)

in which A, $Y_1$ and $Y_2$ are as defined above.

The derivatives of formula (VIII) can be oxidised as described above, the $SCH_3$ group then being converted to the $SOCH_3$ or $SO_2CH_3$ group depending on the amount of oxidising agent used, to give the compounds of formula (I):

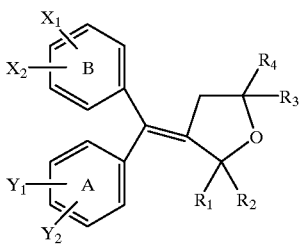

Formula (I)

in which B is a phenyl ring, $X_1$ is $SOCH_3$ or $SO_2CH_3$, $X_2$, $R_1$ and $R_2$ are a hydrogen atom, $R_3R_4$ are an oxygen atom and A, $Y_1$ and $Y_2$ are as defined above.

Reduction of the derivatives of formula (VII), for example with lithium aluminium hydride in tetrahydroftiran, will give the diols of formula (IX):

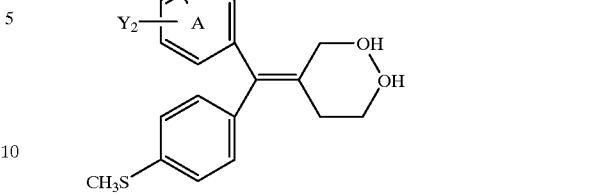

Formula (IX)

in which A, $Y_1$ and $Y_2$ are as defined above.

Dehydration of these diols with sulphuric acid, or by treatment in refluxing toluene in the presence of paratoluenesulphonic acid with a Dean-Stark apparatus, will afford the compounds of formula (I):

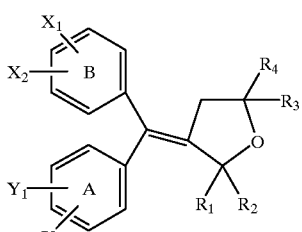

Formula (I)

in which A, $Y_1$ and $Y_2$ are as defined above, B is a phenyl ring, $X_1$ is a 4-$SCH_3$ group and $X_2$, $R_1$, $R_2$, $R_3$ and $R_4$ are a hydrogen atom.

Treatment of these derivatives with an oxidising agent, as described above, will give the corresponding derivatives in which $X_1$ is a 4-$SOCH_3$ or 4-$SO_2CH_3$ group depending on the amount of oxidising agent used.

It is possible to use other preparative variants for the compounds of formula I.

Reaction of the ketone compounds of formula (IV) with ethyl succinate by the Stobbe reaction in tert-butanol in the presence of sodium or potassium tert-butoxide for example, will give the compounds of formula (X):

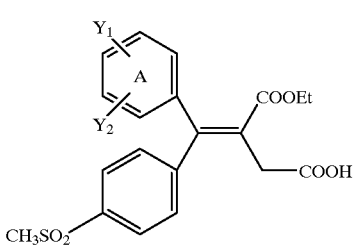

Formula (X)

in which A, $Y_1$ and $Y_2$ are as defined above.

Reduction, this time selective, of the acid group, for example by reaction with borane or the borane/methyl sulphide complex in tetrahydrofuran or diethyl ether, will give the alcohol-esters of formula (XI):

Formula (XI)

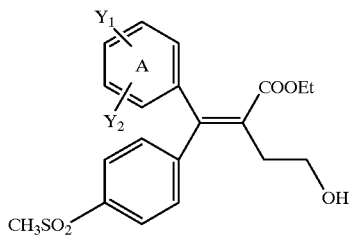

in which A, $Y_1$ and $Y_2$ are as defined above.

These alcohol-esters of formula (XI), or even the corresponding alcohol-acids obtained by hydrolysis of the ester function by sodium hydroxide in refluxing ethanol, will be cyclised by heating in an aromatic solvent, such as toluene for example, in the presence of paratoluenesulphonic acid in order to obtain thie compounds of formula (I):

Formula (I)

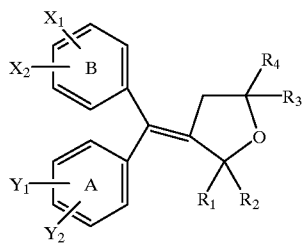

in which A, $Y_1$ and $Y_2$ are as defined above, B is a phenyl ring, $X_1$ is a 4-$SO_2CH_3$ group, $X_2$, $R_3$ and $R_4$ are a hydrogen atom and $R_1R_2$ are an oxygen atom.

The compounds of formula (XII), in which A, $Y_1$ and $Y_2$ are as defined above, may be prepared analogously according to the following reaction scheme, in which Ph is a phenyl group and Z is an MgBr radical when A is a phenyl ring and Li when A is a pyridyl ring:

Formula (XII)

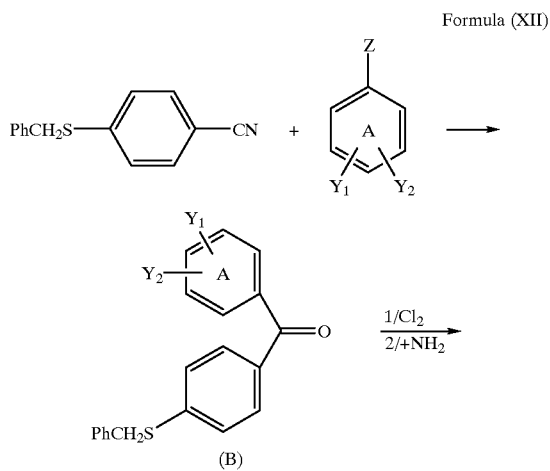

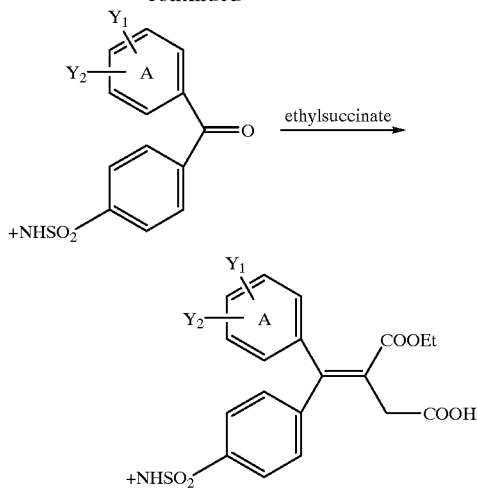

A variant consists of preparing the diarylketone (B) used in the above reaction scheme, by the action of benzylmercaptan $PhCH_2SH$ with a fluorodiarylketone in dimethylformamide in the presence of sodium hydride or sodium carbonate:

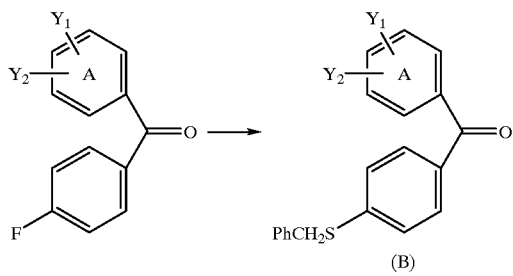

(B)

The compounds of formula (XII) will be treated in the same way as the compounds of formula (X) to give the compounds of formula (I):

Formula (I)

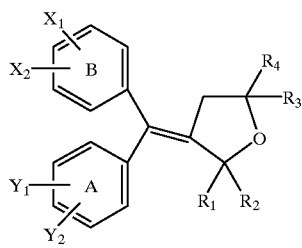

in which B is a phenyl ring, $X_1$ is a 4-$SO_2$NHt-Bu group, $X_2$, $R_3$ and $R_4$ are a hydrogen atom, $R_1R_2$ are an oxygen atom and A, $Y_1$ and $Y_2$ are as defined above. Treatment of these derivatives with a strong acid, for example concentrated sulphuric acid, trifluoroacetic acid or by heating in toluene in the presence of paratoluenesulphonic acid, will give the compounds of formula (I) in which B is a phenyl ring, $X_1$ is a 4-$SO_2NH_2$ group, $X_2$, $R_3$ and $R_4$ are a hydrogen atom, $R_1R_2$ are an oxygen atom and A, $Y_1$ and $Y_2$ are as defined above.

The compounds of formula (I) as defined above are cyclooxygenase-2 inhibitors and possess a very good anti-inflammatory and analgesic activity coupled with an excellent tolerance, particularly gastric tolerance.

These properties justify their application in therapeutics and the invention further relates, by way of drugs, to the products as defined by formula (I) above.

Thus the invention also covers a pharmaceutical composition, characterised in that it comprises a pharmaceutically effective amount of at least one compound of formula (I) as defined above, optionally incorporated in a pharmaceutically acceptable excipient, vehicle or carrier.

These compositions can be administered by the buccal, rectal, parenteral, transdermal, ocular, nasal or auricular route.

These compositions can be solid or liquid and can be presented in the pharmaceutical forms commonly used in human medicine, for example simple or coated tablets, gelatine capsules, granules, suppositories, injectable preparations, transdermal systems, eye lotions, aerosols and sprays, and ear drops. They are prepared by the customary methods. The active principle, which consists of a pharmaceutically effective amount of at least one compound of formula (I) as defined above, can be incorporated therein together with excipients normally employed in pharmaceutical compositions, such as talc, gum Arabic, lactose, starch, magnesium stearate, polyvidone, cellulose derivatives, cocoa butter, semisynthetic glycerides, aqueous or non-aqueous vehicles, fats of animal or vegetable origin, glycols, various wetting agents, dispersants or emulsifiers, silicone gels, certain polymers or copolymers, preservatives, flavourings and colours.

The invention also covers a pharmaceutical composition with anti-inflammatory and analgesic activity which can be used especially as a favourable treatment for inflammatory phenomena and pain, said composition being characterised in that it comprises a pharmaceutically effective amount of at least one compound of formula (I) above in a pharmaceutically acceptable excipient, vehicle or carrier. In one embodiment, a pharmaceutical composition with anti-inflammatory and analgesic activity is prepared which can be used especially as a favourable treatment for various inflammations and pain.

In one variant, a composition is formulated as gelatine capsules or tablets containing a dose of 1 mg to 1000 mg, or as injectable preparations containing a dose of 0.1 mg to 500 mg. It is also possible to use compositions formulated as suppositories, ointments, creams, gels, aerosol preparations, transdermal preparations or plasters.

The invention also covers a method of therapeutic treatment for mammals, characterised in that a therapeutically effective amount of at least one compound of formula (I) as defined above is administered to said mammal. In one variant of this method of treatment, the compound of formula (I), either by itself or in association with a pharmaceutically acceptable excipient, is formulated as gelatine capsules or tablets containing a dose of 1 mg to 1000 mg for oral administration, as injectable preparations containing a dose of 0.1 mg to 500 mg or as suppositories, ointments, creams, gels or aerosol preparations.

This method affords especially a favourable treatment for inflammatory phenomena and pain.

In human and animal therapeutics, the compounds of formula (I) can be administered, by themselves or in association with a physiologically acceptable excipient, in any form, in particular orally in the form of gelatine capsules or tablets, or parenterally in the form of injectable solutions. It is possible to envisage other forms of administration such as suppositories, ointments, creams, gels or aerosol preparations.

As will be clearly apparent from the pharmacological experiments given at the end of the description, the compounds according to the invention can be administered in human therapeutics, in the above-mentioned indications, orally in the form of tablets or gelatine capsules containing a dose of 1 mg to 1000 mg, or parenterally in the form of injectable preparations containing a dose of 0.1 mg to 500 mg, in one or more daily dosage units, for an adult with an average weight of 60 to 70 kg.

In animal therapeutics, the daily dose which can be used is between 0.1 mg and 100 mg per kg.

Further characteristics and advantages of the invention will be understood more clearly from the following Examples, which in no way imply a limitation but are given by way of illustration.

EXAMPLE 1

4-Fluoro-4'-methylthiobenzophenone

Formula (III): A=phenyl, $Y_1$=4-F, $Y_2$=H 86.4 g of aluminium trichloride are added in portions, at a temperature between 0° C. and 5° C., to a solution of 70 g (0.564 mol) of thioanisole and 90.2 g (0.654 mol) of 4-fluorobenzoyl chloride in 500 ml of dichloromethane. When the addition is complete, the mixture is brought back to room temperature and then refluxed for 2 hours. After cooling, the reaction medium is run into an ice/dilute hydrochloric acid mixture and the organic phase is decanted and then dried over magnesium sulphate and evaporated under vacuum to give a residue, which crystallises from diisopropyl ether to give 118 g of 4-fluoro-4'-methylthiobenzophenone melting at 88° C.

EXAMPLE 2

4-Fluoro-4'-methanesulphonylbenzophenone

Formula (IV): A=phenyl, $Y_1$=4-F, $Y_2$=H 87 g of 70% 3-chloroperbenzoic acid are added in portions, at a temperature between 0° C. and 5° C., to a solution of 25 g (0.1015 mol) of 4-fluoro-4'-methylthiobenzophenone, prepared in Example 1, in 350 ml of dichloromethane. The mixture is subsequently stirred at 0° C. for 30 minutes and then brought back to room temperature and stirred for 2 hours 30 minutes. The precipitate obtained is filtered off, washed with dilute sodium hydroxide solution and then dissolved in dichloromethane. The resulting organic phase is dried over magnesium sulphate and evaporated under vacuum to give an oil, which crystallises from diisopropyl ether to give 24.6 g of 4-fluoro-4'-methanesulphonylbenzophenone melting at 136° C.

EXAMPLE 3

3-[1-(4-Fluorophenyl)-1-hydroxy-1-(4-methanesulphonylphenyl)-methyl]dihydrofuran-2-one Formula (VI): A=phenyl, $Y_1$=4-F, $Y_2$=H, $R_3$=$R_4$=H Magnesium turnings (3.5 g) are covered with anhydrous tetrahydrofuran, and a few drops of iodomethane are added. As soon as the reaction has started, a mixture of 24.6 g of 4-fluoro-4'-methanesulphonylbenzophenone and 8.1 ml of α-bromo-γ-butyrolactone in 250 ml of anhydrous tetrahydrofuran is run in dropwise so as to maintain a gentle reflux. When the addition is complete, the reaction medium is cooled and then run into a mixture of ice and 10% dilute sulphuric acid. The organic phase is extracted with tetrahydrofuran, washed with saturated sodium bicarbonate solution and then dried over magnesium sulphate. After evaporation of the solvent, the residue obtained is chromatographed on silica gel with a 9/1 dichloromethane/acetone mixture to give 7 g of 3-[1-(4-fluorophenyl)-1-hydroxy-1-(4-methanesulphonylphenyl)methyl]dihydrofuran-2-one in the form of an amorphous beige powder, which is used as such in the next step.

EXAMPLE 4
(E-3-[1-(4-Fluorophenyl)-1-(4-methanesulphonylphenyl)-methylidene]dihydrofuran-2-one
(E) isomer: Formula (I): A=B=phenyl, $Y_1$=4-F, $X_2$=$Y_2$=H, $X_1$=4-$SO_2CH_3$, $R_1R_2$=O, $R_3$=$R_4$=H A few mg of toluene-4-sulphonic acid are added to a solution of 7 g of 3-[1-(4-fluorophenyl)-1-hydroxy-1-(4-methanesulphonylphenyl)methyl]dihydrofuran-2-one, prepared in Example 3, in 100 ml of toluene and the mixture is refluxed for 10 hours in a Dean-Stark apparatus. The solvent is then evaporated off to dryness under vacuum and the residue is chromatographed using a 9/1 dichloromethanel/acetone mixture as the eluent to give an oil, which is chromatographed using t-butyl methyl ether as the eluent to give 2.9 g of (E)-3-[1-(4-fluorophenyl)-1-(4-methanesulphonylphenyl)methylidene]dihydrofuran-2-one (second product eluted) in the form of crystals melting at 187–9° C. 1.5 g of (Z)-3-[1-(4-fluorophenyl)-1-(4-methanesulphonylphenyl)methylidene]dihydrofuran-2-one (first product eluted) are recovered in the form of crystals melting at 157–158° C.

EXAMPLE 5
4-Chloro-4'-methylthiobenzophenone
Formula (III): A=phenyl, $Y_1$=4-Cl, $Y_2$=H
  Prepared by the procedure of Example 1.
  Crystals melting at 134° C.

EXAMPLE 6
3-[1-(4-Chlorophenyl)-1-hydroxy-1-(4-methylthiophenyl)-methyl]dihydrofuran-2-one
Formula (VI'): A=phenyl, $Y_1$=4-Cl, $Y_2$=H, $R_3$=$R_4$=H A few drops of iodomethane are added to 5.9 g of magnesium turnings covered with anhydrous tetrahydrofuran. As soon as the reaction starts, a mixture of 17 g of 4-chloro-4'-methylthiobenzophenone and 12.6 ml of α-bromo-γ-butyrolactone in 300 ml of anhydrous tetrahydrofuran is added dropwise so as to maintain a gentle reflux. When the addition is complete, the mixture is stirred at room temperature for 1 hour 30 minutes and then cooled with an ice bath. Saturated ammonium chloride solution is subsequently added and the mixture is stirred and then decanted. The organic phase is dried over magnesium sulphate and evaporated under vacuum to give an oily residue which, after chromatography on silica gel in dichloromethane, gives 8.5 g of 3-[1-(4-chlorophenyl)-1-hydroxy-1-(4-methylthiophenyl)methyl]dihydrofuran-2-one in the form of an oil, which is used in the crude state in the next step.

EXAMPLE 7
3-[1-(4-Chlorophenyl)-1-(4-methylthiophenyl)methylidene]-dihydrofuran-2-one
Formula (I): A=B=phenyl, $X_1$=4-Cl, $X_2$=$Y_1$=H, $Y_2$=4-$SCH_3$, $R_1R_2$=O, $R_3$=$R_4$=H 5.2 g of trifluoroacetic anhydride and 3.8 ml of trifluoroacetic acid are added to a solution of 8.6 g of 3-[1-(4-chlorophenyl)-1-hydroxy-1-(4-methylthiophenyl)methyl]dihydrofuran-2-one, prepared in Example 6, in 100 ml of dichloromethane. The mixture is stirred at room temperature for 4 hours and then diluted with water and decanted. The organic phase is dried over magnesium sulphate and evaporated under vacuum to give 7.5 g of 3-[1-(4-chlorophenyl)-1-(4-methylthiophenyl)methylidene]dihydrofuran-2-one in the form of an oil, which is used as such in the next step.

EXAMPLE 8
(Z)-3-[1-(4-Chlorophenyl)-1-(4-methanesulphonylphenyl)-methylidene]dihydrofuran-2-one
(Z) isomer: Formula (I): A=B=phenyl, $Y_1$=4-Cl, $Y_2$=$X_1$=H, $X_2$=4-$SO_2CH_3$, $R_1R_2$=O, $R_3$=$R_4$=H 11 g of sodium perborate trihydrate are added to a solution of 9.5 g of 3-[1-(4-chlorophenyl)-1-(4-methylthiophenyl)methylidene]dihydrofuran-2-one, prepared in Example 7, in 120 ml of acetic acid. The mixture is heated at 40–50° C. for 5 hours and then cooled. The crystals formed are filtered off, washed with water and then chromatographed on silica gel in a dichloromethane/acetone mixture (99/1) to give 4.1 g of (Z)-3-[1-(4-chlorophenyl)-1-(4-methanesulphonylphenyl)methylidene]dihydrofuran-2-one (1st product eluted) in the form of crystals melting at 197–199° C.

Isolation of the second product eluted gives 2.5 g of (E)-3-[1-(4-chlorophenyl)-1-(4-methanesulphonylphenyl)methylidene]dihydrofuran-2-one in the form of crystals melting at 211–212° C.

EXAMPLE 9
3-Fluoro-4'-methylthiobenzophenone
Formula (III): A=phenyl, $Y_1$=3-F, $Y_2$=H
  Prepared by the procedure of Example 1.
  Crystals melting at 76° C.

EXAMPLE 10
3-Fluoro-4'-methanesulphonylbenzophenone
Formula (IV): A=phenyl, $Y_1$=3-F, $Y_2$=H
  Prepared by the procedure of Example 2.
  Crystals melting at 106° C.

EXAMPLE 11
3-Ethoxycarbonyl-4-(3-fluorophenyl)-4-(4-methanesulphonylphenyl)-3-butenoic acid
Formula (X): A=phenyl, $Y_1$=3-F, $Y_2$=H 35.5 g (0.1275 mol) of 3-fluoro-4'-methanesulphonylbenzophenone, prepared in Example 10, are added in portions to a solution of 15.7 g (0.140 mol) of potassium t-butoxide in 100 ml of t-butanol. The mixture is stirred and 32 ml (0.191 mol) of ethyl succinate are added dropwise at a rapid rate. The mixture is subsequently refluxed for 30 minutes and cooled, water and 1 N hydrochloric acid are added to bring the pH to 1 and the mixture is then extracted with t-butyl methyl ether. The organic phase is treated with 2% sodium hydroxide solution and the mixture is decanted. The aqueous phase is acidified with 1 N hydrochloric acid and then extracted with t-butyl methyl ether. The organic phase is dried over magnesium sulphate and evaporated under vacuum to give 39.2 g of 3-ethoxycarbonyl-4-(3-fluorophenyl)-4-(4-methanesulphonylphenyl)-3-butenoic acid in the form of a thick oil, which is used as such in the next step.

EXAMPLE 12
Ethyl 3-(3-fluorophenyl)-3-(4-methanesulphonylphenyl)-2-(2-hydroxyethyl)-2-propenoate
Formula (XI): A=phenyl, $Y_1$=3-F, $Y_2$=H 15.5 ml (0.155 mol) of borane/methyl sulphide complex are added dropwise to a solution of 31.5 g (0.0775 mol) of 3-ethoxycarbonyl-4-(3-fluorophenyl)-4-(4-methanesulphonylphenyl)-3-butenoic acid, prepared in Example 11, in 90 ml of anhydrous tetrahydrofuran. The mixture is stirred at room temperature for 8 hours and 23.5 ml of methanol are added dropwise. The mixture is evaporated to dryness under vacuum and the residue is taken up with ethyl acetate and then treated with an aqueous solution of 7.6 g of potassium carbonate. The organic phase is

EXAMPLE 12 decanted and then dried over magnesium sulphate and evaporated to dryness under vacuum to give 29.3 g of ethyl 3-(3-fluorophenyl)-3-(4-methanesulphonylphenyl)-2-(2-hydroxyethyl)-2-propenoate in the form of a viscous oil, which is used as such in the next step.

EXAMPLE 13
(Z)-3-[1-(3-Fluorophenyl)-1-(4-methanesulphonylphenyl)-methylidene]dihydrofuran-2-one (Z) isomer:Formula (I): A=B=phenyl, $Y_1$=3-F, $X_2$=$Y_2$=H, $X_1$=4-$SO_2CH_3$, $R_1R_2$=O, $R_3$=$R_4$=H 3.3 g of sodium hydroxide dissolved in 10 ml of water are added to a solution of 29.3 g of ethyl 3-(3-fluorophenyl)-3-(4-methanesulphonylphenyl)-2-(2-hydroxyethyl)-2-propenoate, prepared in Example 12, in 50 ml of ethanol and the mixture is refluxed for 2 hours. After evaporation to dryness, the residue is taken up with water, acidified with 1 N hydrochloric acid and then extracted with dichloromethane. The organic phase is dried over magnesium sulphate and evaporated under vacuum to give an oily residue. The oil is solubilized in 150 ml of toluene, and 10 mg of paratoluenesulphonic acid are added. The mixture is refluxed and the water formed is removed with a Dean-Stark apparatus. After cooling, the mixture is washed with water, the organic phase is dried over magnesium sulphate and evaporated under vacuum and the residue is chromatographed on silica in t-butyl methyl ether to give 4 g of (Z)-3-[1-(3-fluorophenyl)-1-(4-methanesulphonylphenyl) methylidene]dihydrofuran-2-one (2nd product eluted) in the form of crystals melting at 153–154° C.

EXAMPLE 14
3,4-Dichloro-4'-methylthiobenzophenone
Formula (III): A=phenyl, $Y_1$=3-Cl, $Y_2$=4-Cl
  Prepared by the procedure of Example 1.
  Crystals melting at 100° C.

EXAMPLE 15
3,4-Dichloro-4'-methanesulphonylbenzophenone
Formula (IV): A=phenyl, $Y_1$=3-Cl, $Y_2$=4-Cl
  Prepared by the procedure of Example 2.
  Crystals melting at 158° C.

EXAMPLE 16
3-Ethoxycarbonyl-4-(3,4-dichlorophenyl)-4-(4-methylsulphonylphenyl)-3-butenoic acid
Formula (X): A=phenyl, $Y_1$=3-Cl, $Y_2$=4-Cl
  Prepared by the procedure of Example 11.
  Oil used as such in the next step.

EXAMPLE 17
Ethyl 3-(3,4-dichlorophenyl)-3-(4-methanesulphonylphenyl)-2-(2-hydroxyethyl)-2-propenoate
Formula (XI): A=phenyl, $Y_1$=3-Cl, $Y_2$=4-Cl
  Prepared by the procedure of Example 12.
  Oil used as such in the next step.

EXAMPLE 18
(Z)-3-[1-(3,4-Dichlorophenyl)-1-(4-methanesulphonylphenyl)-methylidene]dihydrofuran-2-one
(Z) isomer: Formula (I): A=B=phenyl, $Y_1$=3-Cl, $Y_2$=4-Cl, $X_2$=H, $X_1$=4-$SO_2CH_3$, $R_1R_2$=O, $R_3$=$R_4$=H
  Prepared by the procedure of Example 13. Chromatographed in a dichloromethane/acetone mixture (99/1). First product eluted.
  Crystals melting at 195–197° C.
  Isolation of the second product eluted in the chromatography gives the isomer (E)-3-[1-(3,4-dichlorophenyl)-1-(4-methanesulphonylphenyl)methyl-idene]-dihydrofuran-2-one in the form of crystals melting at 163–164° C.

EXAMPLE 19
3-Chloro-4'-methylthiobenzophenone
Formula (III): A=phenyl, $Y_1$=3-Cl, $Y_2$=H
  Prepared by the procedure of Example 1.
  Crystals melting at 70° C.

EXAMPLE 20
3-Chloro-4'-methanesulphonylbenzophenone
Formula (IV): A=phenyl, $Y_1$=3-Cl, $Y_2$=H
  Prepared by the procedure of Example 2.
  Crystals melting at 140° C.

EXAMPLE 21
3-Ethoxycarbonyl-4-(3-chlorophenyl)-4-(4-methanesulphonyl-phenyl)-3-butenoic acid
Formula (X): A=phenyl, $Y_1$=3-Cl, $Y_2$=H
  Prepared by the procedure of Example 11.
  Oil used as such in the next step.

EXAMPLE 22
Ethyl 3-(3-chlorophenyl)-3-(4-methanesulphonylphenyl)-2-(2-hydroxyethyl)-2-propenoate
Formula (M): A=phenyl, $Y_1$=3-Cl, $Y_2$=H
  Prepared by the procedure of Example 12.
  Oil used as such in the next step.

EXAMPLE 23
(Z)-3-[1-(3-Chlorophenyl)-1-(4-methanesulphonylphenyl)-methylidene]dihydrofuran-2-one
(Z) isomer:Formula (I): A=B=phenyl, $Y_1$=3-Cl, $X_2$=$Y_2$=H, $X_1$=4-$SO_2CH_3$, $R_1R_2$=O, $R_3$=$R_4$=H
  Prepared by the procedure of Example 13. Chromatographed in a dichloromethane/acetone mixture (99/1). First product eluted.
  Crystals melting at 147–149° C.
  Isolation of the second product eluted in the chromatography gives the compound (E)-3-[1-(3-chlorophenyl)-1-(4-methanesulphonylphenyl)methyl-idene]-dihydrofuran-2-one in the form of crystals melting at 170–172° C.

EXAMPLE 24
4-Methylthiobenzophenone
Formula (III): A=phenyl, $Y_1$=$Y_2$=H
  Prepared by the procedure of Example 1.
  Crystals melting at 84° C.

EXAMPLE 25
4-Methanesulphonylbenzophenone
Formula (IV): A=phenyl, $Y_1$=$Y_2$=H
  Prepared by the procedure of Example 2.
  Crystals melting at 150° C.

EXAMPLE 26
3-Ethoxycarbonyl-4-phenyl-4-(4-methanesulphonylphenyl)-butenoic acid
Formula (X): A=phenyl, $Y_1$=$Y_2$=H
  Prepared by the procedure of Example 11.
  Oil used as such in the next step.

EXAMPLE 27
Ethyl 3-phenyl-3-(4-methanesulphonylphenyl)-2-(2-hydroxyethyl)-2-propenoate
Formula (XI): A=phenyl, $Y_1$=$Y_2$=H
  Prepared by the procedure of Example 12.
  Oil used as such in the next step.

EXAMPLE 28

(E)-3-[1-Phenyl-1-(4-methanesulphonylphenyl)methylidene]-dihydrofuran-2-one (E) isomer:Formula (I): A=B=phenyl, $Y_1=Y_2=H$, $X_2=H$, $X_1=4-SO_2CH_3$, $R_1R_2=O$, $R_3=R_4=H$ Prepared by the procedure of Example 13.

Chromatographed on silica gel in a dichloromethane/acetone mixture (99/1). First product eluted.

Crystals melting at 135–137° C.

Isolation of the 2nd product eluted gives the isomer (Z)-3-[1-phenyl-1-(4-methanesulphonylphenyl)methylidene]dihydrofuran-2-one in the form of crystals melting at 206–208° C.

EXAMPLE 29

5,5-Dimethyl-3-[1-(4-fluorophenyl)-1-hydroxy-1-(4-methylthiophenyl)methyldihydrofuran-2-one Formula (VI'): A=phenyl, $Y_1=4-F$, $Y_2=H$, $R_3R_4=R_4=CH_3$ 7.5 ml of bromoethane are added dropwise to a suspension of 2.4 g of magnesium turnings in anhydrous diethyl ether. When the addition is complete, the mixture is cooled to 0° C. and 10.5 ml of N,N-diethylamine are added dropwise. The reaction medium is stirred for hour at room temperature and then refluxed for 15 minutes and cooled with a bath of ice and sodium chloride. A solution of 12.3 g of 4-fluoro-4'-methylthiobenzophenone, prepared in Example 1, and 5.7 g of 4,4-dimethylbutyrolactone in 50 ml of anhydrous tetrahydrofuran is added dropwise, the temperature being kept between 0° C. and 5° C. The mixture is then refluxed for 2 hours, cooled and treated with 100 ml of 10% sulphuric acid solution. After extraction with diethyl ether, the organic phase is dried over magnesium sulphate and evaporated under vacuum to give 4.8 g of 5,5-dimethyl-3-[1-(4-fluorophenyl)-1-hydroxy-1-(4-methylthiophenyl)methyl]dihydrofuran-2-one in the form of crystals melting at 185° C.

EXAMPLE 30

5,5-Dimethyl-3-[1-(4-fluorophenyl)-1-(4-methylthiophenyl)-methylidene]dihydrofuran-2-one (E) isomer:Formula (I): A=B=phenyl, $Y_1=4-F$, $Y_2=X_2=H$, $X_1=4SCH_3$, $R_1R_2=O$, $R_3=R_4=CH_3$ (Z) isomer:Formula (I): A=B=phenyl, $X_1=4-F$, $X_2=Y_2=H$, $Y_1=4-SCH_3$, $R_1R_2O$, $R_3=R_4=CH_3$ Prepared by the procedure of Example 4 from the derivative of Example 29.

The two isomers are separated by fractional crystallisation in a diisopropyl ether/pentane mixture:

(E)-5,5-dimethyl-3-[1-(4-fluorophenyl)-1-(4-methylthiophenyl)methylidene]-dihydrofuran-2-one melting at 98° C.

(Z)-5,5-dimethyl-3-[1-(4-fluorophenyl)-1-(4-methylthiophenyl)methylidene]-dihydrofuran-2-one melting at 160° C.

EXAMPLE 31

(E)-5,5-Dimethyl-3-[1-(4-fluorophenyl)-1-(4-methanesulphonylphenyl)methylidene]dihydrofuran-2-one (E) isomer:Formula (I): A=B=phenyl, $Y_1=4-F$, $X_2=Y_2=H$, $X_1=4-SO_2CH_3$, $R_1R_2=O$, $R_3=R_4=CH_3$ 1.9 g of sodium perborate trihydrate are added to a solution of 2 g of (E)-5,5-dimethyl-3-[1-(4-fluorophenyl)-1-(4-methylthiophenyl)methylidene]dihydrofuran-2-one, prepared in Example 30, in 15 ml of acetic acid. The mixture is heated for 3 hours at 45° C. and the crystals formed are filtered off hot and chromatographed on silica gel using a dichloromethane/acetone mixture (9/1) as the eluent to give 1.2 g of (E)-5,5-dimethyl-3-[1-(4-fluorophenyl)-1-(4-methanesulphonylphenyl)methylidene]dihydrofuran-2-one in the form of crystals melting at 175° C.

EXAMPLE 32

5-Ethyl-3-[1-(4-fluorophenyl)-1-hydroxy-1-(4-methylthiophenyl)methyl]dihydrofuran-2-one Formula (VI'): A=phenyl, $Y_1=4-F$, $Y_2=H$, $R_3=C_2H_5$, $R_4=H$ Prepared by the procedure of Example 29 from γ-caprolactone.

Crystals melting at 150° C.

EXAMPLE 33

5-Ethyl-3-[1-(4-fluorophenyl)-1-(4-methylthiophenyl)-methylidene]dihydrofuran-2-one (E) isomer:Formula (I): A=B=phenyl, $Y_1=4-F$, $X_2=Y_2=H$, $X_1=4-SCH_3$, $R_1R_2=O$, $R_3=C_2H_5$, $R_4=H$ (Z) isomer:Formula (I): A=B=phenyl, $X_1=4-F$, $X_2=Y_2=H$, $Y_1=4-SCH_3$, $R_1R_2=O$, $R_3=C_2H_5$, $R_4=H$ Prepared by the procedure of Example 4 from the derivative of Example 32. The mixture of the two isomers, (E) and (Z), is used as such in the next step.

EXAMPLE 34

(E)-5-Ethyl-3-[1-(4-fluorophenyl)-1-(4-methanesulphonylphenyl)methylidene]dihydrofuran-2-one (E) isomer:Formula (I): A=B=phenyl, $Y_1=4-F$, $X_2=X_2=H$, $X_1=4-SO_2CH_3$, $R_1R_2=O$, $R_3=C_2H_5$, $R_4=H$ Prepared by the procedure of Example 31. The isomer (E)-5-ethyl-3-[1-(4-fluorophenyl)-1-(4-methanesulphonylphenyl)methylidene]dihydrofuran-2-one is purified by chromatography on silica gel in a dichloromethane/acetone mixture (99/1) to give crystals melting at 134–136° C. (first product eluted).

Isolation of the second product eluted in the chromatography gives (Z)-5-ethyl-3-[1-(4-fluorophenyl)-1-(4-methanesulphonylphenyl)methylidene]dihydrofuran-2-one in the form of crystals melting at 176–177° C.

EXAMPLE 35

5-Methyl-3-[1-(3-chlorophenyl)-1-hydroxy-1-(4-methylthiophenyl)methyl]dihydrofuran-2-one Formula (VI'): A=phenyl, $Y_1=3-Cl$, $Y_2=H$, $R_3=CH_3$, $R_4=H$ Prepared by the procedure of Example 6 from 3-chloro-4'-methylthiobenzophenone and α-bromo-γ-valerolactone.

Amorphous powder used as such in the next step.

EXAMPLE 36

5-Methyl-3-[1-(3-chlorophenyl)-1-(4-methylthiophenyl)-methylidene]dihydrofuran-2-one (Z) isomer:Formula (I): A=B=phenyl, $Y_1=3-Cl$, $X_2=Y_2=H$, $X_1=4-SCH_3$, $R_1R_2=O$, $R_3=CH_3$, $R_4=H$ (E) isomer:Formula (I): A=B=phenyl, $X_1=3-Cl$, $X_2=Y_2=H$, $Y_1=4-SCH_3$, $R_1R_2=O$, $R_3=CH_3$, $R_4=H$ Prepared by the procedure of Example 4 from the derivative of Example 35. The mixture of the two isomers is used as such, in the form of an oil, in the next step.

EXAMPLE 37

(Z)-5-Methyl-3-[1-(3-chlorophenyl)-1-(4-methanesulphonylphenyl)methyl]dihydrofuran-2-one (Z) isomer:Formula (I): A=B=phenyl, $Y_1=3-Cl$, $X_2=Y_2=H$, $X_1=4-SO_2CH_3$, $R_1R_2=O$, $R_3=CH_3$, $R_4=H$ Prepared by the procedure of Example 31. The isomer (Z)-5-methyl-3-[1-(3-chlorophenyl)-1-(4-methanesulphonylphenyl)methyl]dihydrofuran-2-one is purified by chromatography on silica gel using a dichloromethane/acetone mixture (99/1) as the eluent to give an amorphous powder (first product eluted).

Isolation of the second product eluted gives the isomer (E)-5-methyl-3-[1-(3-chlorophenyl)-1-(4-methanesulphonylphenyl)methyl]dihydrofuran-2-one in the form of crystals melting at 164–165° C.

EXAMPLE 38

2-Chloro-5-(4-methylthiobenzoyl)pyridine
Formula (III): A=3-pyridyl, $Y_1$=6-Cl, $Y_2$=H
Prepared by the procedure of Example 1.
Crystals melting at 145° C.

EXAMPLE 39

2-Chloro-5-(4-methanesulphonylbenzoyl)pyridine
Formula (IV): A=3-pyridyl, $Y_1$=6-Cl, $Y_2$=H
A solution of 34.6 g of 2-chloro-5-(4-methylthiobenzoyl) pyridine, prepared in Example 38, and 42 g of sodium perborate trihydrate in 250 ml of acetic acid is heated for 4 hours at 45° C. The crystals formed are filtered off hot, washed with water and dried to give 32.6 g of 2-chloro-5-(4-methanesulphonylbenzoyl)pyridine in the form of crystals melting at 170° C.

EXAMPLE 40

4-(6-Chloropyridin-3-yl)-3-ethoxycarbonyl-4-(4-methylsulphonylphenyl)-3-butenoic acid
Formula (X): A=3-pyridyl, $Y_1$=6-Cl, $Y_2$=H
Prepared by the procedure of Example 11 from the derivative of Example 39.
Amorphous solid used as such in the next step.

EXAMPLE 41

Ethyl 3-(6-chloropyridin-3-yl)-2-(2-hydroxyethyl)-3-(4-methylsulphonylphenyl)-2-propenoate
Formula (XI): A=3-pyridyl, $Y_1$=6-Cl, $Y_2$=H
Prepared by the procedure of Example 12 from the derivative of Example 40.
Amorphous solid used as such in the next step.

EXAMPLE 42

(Z)-3-[1-(6-Chloropyridin-3-yl)-1-(4-methanesulphonylphenyl)-methylidene]dihydrofuran-2-one
(Z) isomer:Formula (I): A=3-pyridyl, B=phenyl, $Y_1$=6-Cl, $X_2$=$Y_2$=H, $X_1$=4-$SO_2CH_3$, $R_1R_2$=O, $R_3$=$R_4$=H
Prepared by the procedure of Example 13 from the derivative of Example 41.
The (Z) isomer is obtained in the form of crystals melting at 172–174° C. by chromatography in a dichloromethane/acetone mixture (5/1) and then crystallisation from an acetone/ethyl ether mixture.
The isomer (E)-3-[1-(6-chloropyridin-3-yl)-1-(4-methanesulphonylphenyl)methylidene]dihydrofuran-2-one is obtained pure in the form of crystals melting at 198–199° C. by crystallisation from acetone prior to chromatography of the crude mixture of the two isomers.

EXAMPLE 43

3-Ethoxycarbonyl-4-(4-fluorophenyl)-4-(4-methanesulphonylphenyl)-3-butenoic acid
Formula (X): A=phenyl, $Y_1$=4-F, $Y_2$=H
Prepared by the procedure of Example 11 from the 4-fluoro-4'-methanesulphonylbenzophenone prepared in Example 2.
Oil used as such in the next step.

EXAMPLE 44

4-[1-(4-Fluorophenyl)-1-(4-methanesulphonylphenyl) methylidene]-dihydrofuran-2-one
Formula (I): A=B=phenyl, $X_1$=4-$SO_2CH_3$, $X_2$=$Y_2$=H, $Y_1$=4-F, $R_1R_2$=H, $R_3R_4$=O 13.6 g of powdered anhydrous calcium chloride are added to a solution of 3-ethoxycarbonyl-4-(4-fluorophenyl)-4-(4-methanesulphonylphenyl)-3-butenoic acid, prepared in Example 43, in 500 ml of ethanol. The mixture is stirred at room temperature and a solution of 7.5 g of sodium borohydride in a mixture composed of 1.5 g of potassium hydroxide, 10 ml of water and 10 ml of ethanol is added dropwise while cooling with an ice bath. After 4 hours at room temperature, the reaction medium is cooled to 0° C. and 6 N hydrochloric acid solution is added dropwise. After extraction with dichloromethane, the organic phase is dried over magnesium sulphate and evaporated under vacuum and the residue is crystallised from isopropyl ether. The crystals obtained are recrystallized from methanol to give 5 g of 4-[1-(4-fluorophenyl)-1-(4-methanesulphonylphenyl) methylidene]-dihydrofuran-2-one in the form of a mixture (50/50) of the two isomers, (E) and (Z), which are crystals melting at 160–164° C.

EXAMPLE 45

3-Methyl-4'-methylthiobenzophenone
Formula (III): A=phenyl, $Y_1$=3-$CH_3$, $Y_2$=H
Prepared by the procedure of Example 1.
Crystals melting at 46–47° C.

EXAMPLE 46

3-Methyl-4'-methanesulphonylbenzophenone
Formula (IV): A=phenyl, $Y_1$=3-$CH_3$, $Y_2$=H
Prepared by the procedure of Example 2.
Crystals melting at 150° C.

EXAMPLE 47

3-Ethoxycarbonyl-4-(3-methylphenyl)-4-(4-methanesulphonylphenyl)-3-butenoic acid
Formula (X): A=phenyl, $Y_1$=3-$CH_3$, $Y_2$=H
Prepared by the procedure of Example 11 from the derivative of Example 46.
Oil used as such in the next step.

EXAMPLE 48

Ethyl 3-(3-methylphenyl)-3-(4-methanesulphonylphenyl)-2-(2-hydroxyethyl)-2-propenoate
Formula (X): A=phenyl, $Y_1$=3-$CH_3$, $Y_2$=H
Prepared by the procedure of Example 12 from the derivative of Example 47.
Oil used as such in the next step.

EXAMPLE 49

(Z)-3-[1-(3-Methylphenyl)-1-(4-methanesulphonylphenyl)-methylidene]dihydrofuran-2-one
(Z) isomer:Formula (I): A=B=phenyl, $Y_1$=3-$CH_3$, $X_2$=$Y_2$=H, $X_1$=4-$SO_2CH_3$, $R_1R_2$=O, $R_3$=$R_4$=H
Prepared by the procedure of Example 13 from the derivative of Example 48.
Purified by chromatography on silica gel in a dichloromethane/acetone mixture (99/1). First product eluted in the form of crystals melting at 166° C.

EXAMPLE 50

3,4-Difluoro-4'-methylthiobenzophenone
Formula (III): A=phenyl, $Y_1$=3-F, $Y_2$=4-F
Prepared by the procedure of Example 1.
Crystals melting at 96° C.

EXAMPLE 51

3,4-Difluoro-4'-methanesulphonylbenzophenone
Formula (IV): A=phenyl, $Y_1$=3-F, $Y_2$=4-F
Prepared by the procedure of Example 2 from the derivative of Example 50.
Crystals melting at 120° C.

EXAMPLE 52
3-Ethoxycarbonyl-4-(3,4-difluorophenyl)-4-(4-methanesulphonylphenyl)-3-butenoic acid
Formula (X): A=phenyl, $Y_1$=3-F, $Y_2$=4-F Prepared by the procedure of Example 11 from the derivative of Example 51.

Oil used as such in the next step.

EXAMPLE 53
Ethyl 3-(3,4-difluorophenyl)-3-(4-methanesulphonylphenyl)-2-(2-hydroxyethyl)-2-propenoate
Formula (XI): A=phenyl, $Y_1$=3-F, $Y_2$=4-F Prepared by the procedure of Example 12 from the derivative of Example 52.

Oil used as such in the next step.

EXAMPLE 54
(Z)-3-[1-(3,4-Difluorophenyl)-1-(4-methanesulphonylphenyl)-methylidene]dihydrofuran-2-one
(Z) isomer:Formula (I): A=B=phenyl, $Y_1$=3-F, $Y_2$=4-F, $X_1$=4-$SO_2CH_3$, $X_2$=H, $R_1R_2$=O, $R_3$=$R_4$=H Prepared by the procedure of Example 13 from the derivative of Example 53.

Purified by chromatography on silica gel in a dichloromethane/acetone mixture (99/1). First product eluted. Crystals melting at 148° C.

EXAMPLE 55
4-Benzylthiobenzonitrile

A mixture of 37.2 g of benzylmercaptan, 36.3 g of 4-fluorobenzonitrile and 42 g of potassium carbonate in 700 ml of 2-butanone is refluxed for 7 hours. The solvent is evaporated off under vacuum and the residue is taken up with water and petroleum ether. The crystals formed are filtered off and washed with water and petroleum ether to give 46 g of 4-benzylthiobenzonitrile in the form of crystals melting at 85° C.

EXAMPLE 56
4-Benzylthio-4'-fluorobenzophenone

A solution of 44 ml of 4-bromo-1-fluorobenzene in 300 ml of anhydrous diethyl ether is added dropwise to a suspension of 9.6 g of magnesium turnings in 20 ml of anhydrous diethyl ether. When the addition is complete, the mixture is stirred for a few minutes at room temperature and a solution of 46 g of 4-benzylthiobenzonitrile, prepared in Example 55, in 400 ml of anhydrous tetrahydrofuran is added dropwise. The diethyl ether is distilled and the mixture is refluxed for 3 hours and then cooled with ice. 6 N hydrochloric acid solution (400 ml) is added dropwise and the mixture is refluxed for 6 hours. After the addition of water and dichloromethane, the organic phase is decanted, dried over magnesium sulphate and then evaporated under vacuum. The residue crystallises from diisopropyl ether to give 48 g of 4-benzylthio-4'-fluorobenzophenone in the form of crystals melting at 96° C.

EXAMPLE 57
4-t-Butylaminosulphonyl-4'-fluorobenzophenone

Chlorine is bubbled up to the saturation point (36 g) into a solution of 43 g of 4-benzylthio-4'-fluorobenzophenone, prepared in Example 56, in 300 ml of acetic acid cooled to 0° C. The mixture is subsequently stirred for 2 hours at room temperature and then poured into iced water and extracted with dichloromethane. The organic phase is washed with water, dried over magnesium sulphate and evaporated under vacuum to give 47 g of an oil, which is dissolved in 100 ml of 1,2-dichloroethane. This solution is added dropwise to a solution of 50 ml of t-butylamine in 300 ml of 1,2-dichloroethane. The mixture is heated for one hour at 80° C., cooled and washed with water and then with dilute hydrochloric acid. The organic phase is dried over magnesium sulphate and evaporated under vacuum. The residue crystallises from diethyl ether to give 25 g of 4-t-butylaminosulphonyl-4'-fluorobenzophenone in the form of crystals melting at 160° C.

EXAMPLE 58
3-Ethoxycarbonyl-4-(4-t-butylaminosulphonylphenyl)-4-(4-fluorophenyl)-3-butenoic acid
Formula (XII): A=phenyl, $Y_1$=4-F, $Y_2$=H Prepared by the procedure of Example 11 from the derivative of Example 57 using 2 equivalents of potassium tert-butoxide.

Amorphous powder used as such in the next step.

EXAMPLE 59
Ethyl 3-(4-t-butylaminosulphonylphenyl)-3-(4-fluorophenyl)-2-(2-hydroxyethyl)-2-propenoate Prepared by the procedure of Example 12 from the derivative of Example 58.

The oil obtained is taken up with diethyl ether and the crystals formed are dried to give the pure isomer ethyl (Z)-3-(4-t-butylaminosulphonylphenyl)-3-(4-fluorophenyl)-2-(2-hydroxyethyl)-2-propenoate in the form of crystals melting at 152° C. The filtrate is evaporated under vacuum to give an oily residue corresponding to the isomer ethyl (E)-3-(4-t-butylaminosulphonylphenyl)-3-(4-fluorophenyl)-2-(2-hydroxyethyl)-2-propenoate, which is used as such in the next step.

EXAMPLE 60
(E)-4-[(4-fluorophenyl)-(2-oxo-dihydrofuran-3-ylidene)methyl]benzenesulphonamide
(E) isomer:Formula (I): A=B=phenyl, $Y_1$=4-F, $Y_2$=$X_2$=H $X_1$=4-$SO_2NH_2$, $R_1R_2$=O, $R_3$=$R_4$=H Ethyl (E)-3-(4-t-butylaminosulphonylphenyl)-3-(4-fluorophenyl)-2-(2-hydroxyethyl)-2-propenoate (10 g), prepared in Example 59, is dissolved in 20 ml of ethanol, and a solution of 2 g of sodium hydroxide in 10 ml of water is added. The mixture is refluxed for 2 h. After evaporation to dryness, the residue is taken up with water, acidified with 1 N hydrochloric acid and then extracted with dichloromethane. The organic phase is dried over magnesium sulphate and then evaporated under vacuum. The residue is added in portions to 500 ml of concentrated sulphuric acid. The mixture is stirred for 15 minutes at room temperature and then poured into iced water and the crystals formed are filtered off, washed with diethyl ether and then taken up with 100 ml of warm acetone. 50 ml of diethyl ether are added to the solution obtained and the crystals formed are filtered off and dried to give 6 g of (E)-3-[1-(4-aminosulphonylphenyl)-1-(4-fluorophenyl)methylidene]dihydrofuran-2-one in the form of crystals melting at 202° C.

EXAMPLE 61
(Z)-4-1(4-fluorophenyl)-(2-oxo-dihydrofuran-3-ylidene)methyl]benzenesulphonamide
(Z) isomer:Formula (I): A=B=phenyl, $X_1$=4-F, $X_2$=$Y_2$=H, $Y_1$=4-$SO_2N_2$, $R_1R_2$=O, $R_3$=$R_4$=H Prepared by the procedure of Example 60 from the (Z) isomer prepared in Example 59.

Crystals melting at 222° C.

EXAMPLE 62
4-chloro-4'-methanesulphonylbenzophenone
Formula (IV): A=phenyl, $Y_1$=4-Cl, $Y_2$=H
Prepared by the procedure of Example 39 from the derivative of Example 5.
Crystals melting at 176° C.

EXAMPLE 63
(Z)-3-ethoxycarbonyl-4-(4-chlorophenyl)-4-(4-methanesulphonyl)-3-butenoic acid
Formula (X): A=phenyl, $Y_1$=4-Cl, $Y_2$=H
To a suspension of 20 g of 4-chloro-4'-methanesulphonylbenzophenone, prepared in Example 62, in 100 ml of t-butanol are added at once 7.2 g of sodium t-butoxide at room temperature. The suspension is heated at 40° C. and a solution of 16.9 ml of ethyl succinate in 20 ml of t-butanol is added over 10 minutes. The temperature is kept at 55° C. for 30 minutes and then brought to 35–40° C.; 140 ml of cold water are added and the mixture is stirred for 30 minutes. The solution is filtered and the crystals are washed with water. The aqueous alcohol phase is washed twice with 75 ml of toluene and then acidified with concentrated hydrochloric acid. The crystals are filtered off, washed with water and dried under vacuum to give 20.2 g of (Z)-3-ethoxycarbonyl-4-(4-chlorophenyl)-4-(4-methanesulphonyl)-3-butenoic acid, HPLC purity: 81.6%, 12.1% (E) isomer. Recrystallisation from propan-2-ol allows obtaining 14 g of (Z)-3-ethoxycarbonyl-4-(4-chlorophenyl)-4-(4-methanesulphonyl)-3-butenoic acid of HPLC purity: 96.1% containing 0.7% of the (E) isomer, in the form of crystals melting at 183° C.

EXAMPLE 64
Ethyl (Z)-3-(4-chlorophenyl)-3-(4-methanesulphonylphenyl)-2-(2-hydroxyethyl)-2-propenoate
Formula (XI): A=phenyl, $Y_1$=4-Cl, $Y_2$=H
To a solution of 350 g of (Z)-3-ethoxycarbonyl-4-(4-chlorophenyl)-4-4-methanesulphonylphenyl)-3-butenoic acid, prepared in Example 63, in 1.5 l of tetrahydrofuran are added dropwise, and with good stirring, 120 ml of borane/dimethyl sulphide complex. At the end of the addition, the solution is stirred for 2.5 hours at room temperature. The borane in excess is hydrolysed with 100 ml of methanol and 100 ml of water. After evaporation of the solvent under vacuum, the residue is crystallised in water, filtered and washed with water to give ethyl (Z)-3-(4-chlorophenyl)-3-(4-methanesulphonylphenyl)-2-(2-hydroxyethyl)-2-propenoate in the form of moist crystals which are used as such in the next step. By drying these crystals and recrystallising them in propan-2-ol, ethyl (Z)-3-4-chlorophenyl)-3-(4-methanesulphonylphenyl)-2-(2-hydroxyethyl)-2-propenoate is obtained in the form of crystals of HPLC purity 98.3% and of melting point 128° C.

EXAMPLE 65
(Z)-3-[1-(4-chlorophenyl)-1-(4-methanesulphonylphenyl) methylidene]-dihydro-furan-2-one
Formula (I): A=B=phenyl, $Y_1$=4-Cl, $X_2$=$Y_2$=H, $X_1$=4-$SO_2CH_3$, $R_1R_2$=O, $R_3$=$R_4$=H
The moist product from Example 64 is heated under reflux in 1.5 l of toluene in the presence of 1 g of paratoluenesulphonic acid. The water and ethanol are removed with the aid of a Dean Stark apparatus and then about 1 l of toluene is evaporated off. After returning to room temperature, the crystals formed are filtered off and washed with animal amount of butane-2-one, then dried to give 261.5 g of (Z)-3-[1-(4-chlorophenyl)-1-(4-methanesulphonylphenyl)methylidene]-dihydro-furan-2-one in the form of crystals melting at 188–190° C.

EXAMPLE 66
3,5-dichloro-4'-methylthiobenzophenone
Formula (III),: A=phenyl, $Y_1$=3-Cl, $Y_2$=5-Cl
Prepared by the procedure of Example 1.
Crystals melting at 108° C.

EXAMPLE 67
3,5-dichloro-4'-methanesulphonylbenzophenone
Formula (IV): A=phenyl, $Y_1$=3-Cl, $Y_2$=5-Cl
Prepared by the procedure of Example 39.
Crystals melting at 200° C.

EXAMPLE 68
(Z)-3-ethoxycarbonyl-4-(3,5-dichlorophenyl)-4-(4-methanesulphonylphenyl)-3-butenoic acid
(Z) isomer:Formula (X): A=phenyl, $Y_1$=3-Cl, $Y_2$=5-Cl
Prepared by the procedure of Example 1.
Crystals melting at 180° C.

EXAMPLE 69
Ethyl (Z)-3-(3,5-dichlorophenyl)-3-(4-methanesulphonylphenyl)-2-(2-hydroxyethyl)-2-propenoate
(Z) isomer:Formula (XI): A=phenyl, $Y_1$=3-Cl, $Y_2$=5-Cl
Prepared by the procedure of Example 12.
Oil used as such in the next step.

EXAMPLE 70
(Z)-3-[1-(3,5-dichlorophenyl)-1-(4-methanesulphonylphenyl) methylidene]-dihydro-furan-2-one
(Z) isomer:Formula (I): A=B=phenyl, $Y_1$=3-Cl, $Y_2$=5-Cl, $X_1$=4-$SO_2CH_3$, $X_2$=H, $R_1R_2$=O, $R_3$=$R_4$=H
Prepared by the procedure of Example 65.
Crystals melting at 114° C.

EXAMPLE 71
2,4-difluoro-4'-methylthiobenzophenone
Formula (III): A=phenyl, $Y_1$=2-F, $Y_2$=4-F
Prepared by the procedure of Example 1.
Crystals melting at 98° C.

EXAMPLE 72
2,4-difluoro-4'-methanesulphonylbenzophenone
Formula (IV): A=phenyl, $Y_1$=2-F, $Y_2$=4-F
Prepared by the procedure of Example 39.
Crystals melting at 160° C.

EXAMPLE 73
3-ethoxycarbonyl-4-(2,4-difluorophenyl)-4-(4-methanesulphonylphenyl)-3-butenoic acid
Formula (X): A=phenyl, $Y_1$=2-F, $Y_2$=4-F
Prepared by the procedure of Example 11.
Oil used as such in the next step.

EXAMPLE 74
Ethyl 3-(2,4-difluorophenyl)-3-(4-methanesulphonylphenyl)-2-(2-hydroxyethyl)-2-propenoate
Formula (XI): A=phenyl, $Y_1$=2-F, $Y_2$=4-F
Prepared by the procedure of Example 12.
Oil used as such in the next step.

EXAMPLE 75
(Z)-3-[1-(2,4-difluorophenyl)-1-(4-methanesulphonylphenyl) methylidene]-dihydro-furan-2-one
(Z) isomer:Formula (I): A=B=phenyl, $Y_1$=2-F, $Y_2$=4-F, $X_1$=4-$SO_2CH_3$, $X_2$=H, $R_1R_2$=O, $R_3$=$R_4$=H
Prepared by the procedure of Example 65, purified by chromatography in a dichloromethane/acetone mixture (10/0.3).
Crystals melting at 140° C.

EXAMPLE 76

3,5-difluoro-4'-methylthiobenzophenone
Formula (III): A=phenyl, $Y_1$=3-F, $Y_2$=5-F
   Prepared by the procedure of Example 1.
   Crystals melting at 90° C.

EXAMPLE 77

3,5-difluoro-4'-methanesulphonylbenzophenone
Formula (IV): A=phenyl, $Y_1$=3-F, $Y_2$=5-F
   Prepared by the procedure of Example 39.
   Crystals melting at 152° C.

EXAMPLE 78

3-ethoxycarbonyl-4-(3,5-difluorophenyl)-4-(4-methanesulphonylphenyl)-3-butenoic acid
Formula (X): A=phenyl, $Y_1$=3-F, $Y_2$=5-F
   Prepared by the procedure of Example 11.
   Oil used as such in the next step.

EXAMPLE 79

Ethyl 3-(3,5-difluorophenyl)-3-(4-methanesulphonylphenyl)-2-(2-hydroxyethyl)-2-propenoate
Formula (XI): A=phenyl, $Y_1$=3-F, $Y_2$=5-F
   Prepared by the procedure of Example 12.
   Oil used as such in the next step.

EXAMPLE 80

(Z)-3-[1-(3,5-difluorophenyl)-1-(4-methanesulphonylphenyl) methylidene]-dihydro-furan-2-one
(Z) isomer:Formula (I): A=B=phenyl, $Y_1$=3-F, $Y_2$=5-F, $X_1$=4-$SO_2CH_3$, $X_2$=H, $R_1R_2$=O, $R_3$=$R_4$=H
   Prepared by the procedure of Example 65, purified by chromatography in a dichloromethane/acetone mixture (10/0.3).
   Crystals melting at 162° C.

EXAMPLE 81

4-methyl-4'-methylthiobenzophenone
Formula (III): A=phenyl, $Y_1$=4-$CH_3$, $Y_2$=H
   Prepared by the procedure of Example 1.
   Crystals melting at 96° C.

EXAMPLE 82

4-methyl-4'-methanesulphonylbenzophenone
Formula (IV): A=phenyl, $Y_1$=4-$CH_3$, $Y_2$=H
   Prepared by the procedure of Example 39.
   Crystals melting at 180° C.

EXAMPLE 83

3-ethoxycarbonyl-4-(4-methylphenyl)-4-(4-methanesulphonylphenyl)-3-butenoic acid
Formula (X): A=phenyl, $Y_1$=4-$CH_3$, $Y_2$=H
   Prepared by the procedure of Example 11.
   Oil used as such in the next step.

EXAMPLE 84

Ethyl 3-(4-methylphenyl)-3-(4-methanesulphonylphenyl)-2-(2-hydroxyethyl)-2-propenoate
Formula (XI): A=phenyl, $Y_1$=4-$CH_3$, $Y_2$=H
   Prepared by the procedure of Example 12.
   Oil used as such in the next step.

EXAMPLE 85

(E)-3-[1-(4-methylphenyl)-1-(4-methanesulphonylphenyl) methylidene]-dihydro-furan-2-one
(E) isomer:Formula (I): A=B=phenyl, $Y_1$=4-$CH_3$, $Y_2$=H, $X_1$=4-$SO_2CH_3$, $X_2$=H, $R_1R_2$=O, $R_3$=$R_4$=H
   Prepared by the procedure of Example 65, purified by chromatography in a dichloromethane/acetone mixture (10/0.3).
   Crystals melting at 222° C.

EXAMPLE 86

3-bromo -4'-methylthiobenzophenone
Formula (III): A=phenyl, $Y_1$=3-Br, $Y_2$=H
   Prepared by the procedure of Example 1.
   Crystals melting at 90° C.

EXAMPLE 87

3-bromo-4'-methanesulphonzobenzophenone
Formula (IV): A=phenyl, $Y_1$=3-Br, $Y_2$=H
   Prepared by the procedure of Example 39.
   Crystals melting at 170° C.

EXAMPLE 88

3-ethoxycarbonyl-4-(3-bromophenyl)-4-(4-methanesulphonylphenyl)-3-butenoic acid
Formula (X): A=phenyl, $Y_1$=3-Br, $Y_2$=H
   Prepared by the procedure of Example 11.
   Oil used as such in the next step.

EXAMPLE 89

Ethylyl-(3-bromophenyl)-3-(4-methanesulphonylphenyl)-2-(2-hydroxyethyl)-2-propenoate
Formula (XI): A=phenyl, $Y_1$=3-Br, $Y_2$=H
   Prepared by the procedure of Example 12.
   Oil used as such in the next step.

EXAMPLE 90

(Z)-3-[1-(3-bromophenyl)-1-(4-methanesulphonylphenyl) methylidene]-dihydro-furan-2-one
(Z) isomer:Formula (I): A=B=phenyl, $Y_1$=3-Br, $Y_2$=H, $X_1$=4-$SO_2CH_3$, $X_2$=H, $R_1R_2$=O, $R_3$=$R_4$=H
   Prepared by the procedure of Example 65, purified by chromatography in a dichloromethanelacetone mixture (10/0.3).
   Crystals melting at 162° C.

EXAMPLE 91

3-chloro-4-fluoro-4'-methylthiobenzophenone
Formula (III): A=phenyl, $Y_1$=3-Cl, $Y_2$=4-F
   Prepared by the procedure of Example 1.
   Crystals melting at 116° C.

EXAMPLE 92

3-chloro-4-fluoro-4'-methanesulphonylbenzophenone
Formula (IV): A=phenyl, $Y_1$=3-Cl, $Y_2$=4-F
   Prepared by the procedure of Example 39.
   Crystals melting at 146° C.

EXAMPLE 93

3-ethoxycarbonyl-4-(3-chloro-4-fluorophenyl)-4-(4-methanesulphonylphenyl)-3-butenoic acid
Formula (X): A=phenyl, $Y_1$=3-Cl, $Y_2$=4-F
   Prepared by the procedure of Example 11.
   Oil used as such in the next step.

EXAMPLE 94

Ethyl 3-(3chloro-4-fluorophenyl)-3-(4-methanesulphonylphenyl)-2-(2-hydroxyethyl)-2-propenoate
Formula (XI): A=phenyl, $Y_1$=3-Cl, $Y_2$=4-F
   Prepared by the procedure of Example 12.
   Oil used as such in the next step.

EXAMPLE 95
(Z)-3-[1-(3-chloro-4-fluorophenyl)-1-(4-methanesulphonylphenyl)methylidene]-dihydrofuran-2-one (Z) isomer:Formula (I): A=B=phenyl, $Y_3$=3-Cl, $Y_2$=4-F, $X_1$=4-$SO_2CH_3$, $X_2$=H, $R_1R_2$=O, $R_3$=$R_4$=H Prepared by the procedure of Example 65, purified by chromatography in a dichloromethane/acetone mixture (10/0.3).

Crystals melting at 123° C.

EXAMPLE 96
2-bromo-4'-methylthiobenzophenone

Formula (III): A=phenyl, $Y_1$=4-Br, $Y_2$=H

Prepared by the procedure of Example 1.

Crystals melting at 148° C.

EXAMPLE 97
4-bromo-4'-methanesulphonylbenzophenone

Formula (IV): A=phenyl, $Y_1$=4-Br, $Y_2$=H

Prepared by the procedure of Example 39.

Crystals melting at 188° C.

EXAMPLE 98
3-ethoxycarbonyl-4-(4-bromophenyl)-4-(4-methanesulphonylphenyl)-3-butenoic acid Formula (X): A=phenyl, $Y_1$=4-Br, $Y_2$=H Prepared by the procedure of Example 11.

Oil used as such in the next step.

EXAMPLE 99
Ethyl 3-(4-bromophenyl)-3-(4-methanesulphonylphenyl)-2-(2-hydroxyethyl)-2-propenoate Formula (XI): A=phenyl, $Y_1$=4-Br, $Y_2$=H Prepared by the procedure of Example 12.

Oil used as such in the next step.

EXAMPLE 100
(Z)-3-[1-(4-bromophenyl)-1-(4-methanesulphonylphenyl)methylidene]-dihydro-furan-2-one (Z) isomer:Formula (I): A=B=phenyl, $Y_1$=4-Br, $Y_2$=H, $X_1$=4-$SO_2CH_3$, $X_2$=H, $R_1R_2$=O, $R_3$=$R_4$=H Prepared by the procedure of Example 65, purified by chromatography in a dichloromethanelacetone mixture (10/0.3).

Crystals melting at 204° C.

EXAMPLE 101
2-(4methylthiobenzoyl)furan

Formula (III): A=2-furyl, $Y_1$=$Y_2$=H

Prepared by the procedure of Example 1.

Crystals melting at 86° C.

EXAMPLE 102
2-(4-methanesulphonylbenzoyl)furan

Formula (IV): A=2-furyl, $Y_1$=$Y_2$=H

Prepared by the procedure of Example 39.

Crystals melting at 112° C.

EXAMPLE 103
3-ethoxycarbonyl-4-(furan-2-yl)-4-(4-methanesulphonylphenyl)-3-butenoic acid Formula (X): A=2-furyl, $Y_1$=$Y_2$=H Prepared by the procedure of Example 11.

Oil used as such in the next step.

EXAMPLE 104
Ethyl 3-(furan-2-yl)-3-(4-methanesulphonylphenyl)-2-(2-hydroxyethyl)-2-propenoate Formula (XI): A=2-furyl, $Y_1$=$Y_2$=H Prepared by the procedure of Example 12.

Oil used as such in the next step.

EXAMPLE 105
(Z)-3-[1-(furan-2-yl)-1-(4-methanesulphonylphenyl)methylidene]-dihydro-furan-2-one (Z) isomer:Formula (I): A=2-furyl, B=phenyl, $Y_1$=$Y_2$=H, $X_1$=4-$SO_2CH_3$, $X_2$=H, $R_1R_2$=O, $R_3$=$R_4$=H Prepared by the procedure of Example 65, purified by chromatography in a dichloromethane/acetone mixture (10/0.3).

Crystals melting at 170° C.

EXAMPLE 106
(4-methylthiobenzoyl)cyclohexane

Formula (III): A=cyclohexyl, $Y_1$=$Y_2$=H

Prepared by the procedure of Example 1.

Crystals melting at 110° C.

EXAMPLE 107
(4-methanesulphonylbenzoyl)cyclohexane

Formula (IV): A=cyclohexyl, $Y_1$=$Y_2$=H

Prepared by the procedure of Example 39.

Crystals melting at 116° C.

EXAMPLE 108
3-ethoxycarbonyl-4-cyclohexyl-4-(4-methane sulphonylphenyl)-3-butenoic acid Formula (X): A=cyclohexyl, $Y_1$=$Y_2$=H Prepared by the procedure of Example 11.

Oil used as such in the next step.

EXAMPLE 109
Ethyl 3-cyclohexyl-3-(4-methanesulphonylphenyl)-2-(2-hydroxyethyl)-2-propenoate Formula (XI): A=cyclohexyl, $Y_1$=$Y_2$=H Prepared by the procedure of Example 12.

Oil used as such in the next step.

EXAMPLE 110
(Z)-3-[1-cyclohexyl-1-(4-methanesulphonylphenyl)-methylidene]-dihydro-furan-2-one (Z) isomer:Formula (I): A=cyclohexyl, B=phenyl, $Y_1$=$Y_2$=H, $X_1$=4$SO_2CH_3$, $X_2$=H, $R_1R_2$=O, $R_3$=$R_4$=H Prepared by the procedure of Example 65.

Crystals melting at 148° C.

EXAMPLE 111
3-fluoro-4-methyl-4'-methylthiobenzophenone

Formula (III): A=phenyl, $Y_1$=3-F, $Y_2$=4-$CH_3$

To a suspension of 6.4 g of magnesium turnings in 5 ml of anhydrous diethyl ether is added dropwise a solution of 50 g of 4-bromo-2-fluorotoluene in 150 ml of anhydrous diethyl ether. At the end of the addition, the mixture is stirred for 30 minutes and then a solution of 4-methylthiobenzonitrile in 200 ml of anhydrous tetrahydrofuran is added. The diethyl ether is distilled and the mixture is then heated under reflux for 4 hours. After returning to room temperature, 300 ml of 6N hydrochloric acid are added dropwise. The mixture is then heated under reflux for 6 hours and then cooled to room temperature and extracted with diisopropyl ether. The organic phase is dried over magnesium sulphate and then evaporated to dryness. The residue crystallises in diethyl ether giving 25 g of 3-fluoro-4-methyl-4'-methylthiobenzophenone in the form of crystals melting at 94° C.

EXAMPLE 112
3-fluoro-4-methyl-4'-methanesulphonylbenzophenone
Formula (IV): A=phenyl, $Y_1$=3-F, $Y_2$=4-$CH_3$
Prepared by the procedure of Example 39.
Crystals melting at 170° C.

EXAMPLE 113
(Z)-3-ethoxycarbonyl-4-(3-fluoro-4-methylphenyl)-4-(4-methanesulphonylphenyl)-3-butenoic acid
Formula (X): A=phenyl, $Y_1$=3-F, $Y_2$=4-$CH_3$
Prepared by the procedure of Example 11, purified by treatment of the crude mixture of both (E) and (Z) isomers with 1 equivalent of D-(+)-α-methylbenzylamine in 5 volumes of ethyl acetate. The crystals formed are removed ((E) isomer salt) and the filtrate is acidified with dilute hydrochloric acid, separated and evaporated under vacuum to give an oil corresponding to the (Z) isomer containing less than 5% of the (E) isomer.

EXAMPLE 114
Ethyl (Z)-3-(3-fluoro-4-methylphenyl)-3-(4-methanesulphonylphenyl)-2-(2-hydroxyethyl)-2-propenoate
Formula (XI): A=phenyl, $Y_1$=3-F, $Y_2$=4-$CH_3$
Prepared by the procedure of Example 12.
Oil used as such in the next step.

EXAMPLE 115
(Z)-3-[1-(3-fluoro-4-methylphenyl)-1-(4-methanesulphonylphenyl)methylidene]-dihydro-furan-2-one
(Z)isomer:Formula (I): A=B=phenyl, $Y_1$=3-F, $Y_2$=4-$CH_3$, $X_1$=4-$SO_2CH_3$, $X_2$=H, $R_1R_2$=O, $R_3$=$R_4$=H
Prepared by the procedure of Example 65.
Crystals melting at 169–170° C.

EXAMPLE 116
4-trifluoromethyl-4'-methylthiobenzophenone
Formula (III): A=phenyl, $Y_1$=4-$CF_3$, $Y_2$=H,
Prepared by the procedure of Example 1.
Crystals melting at 139° C.

EXAMPLE 117
4-trifluoromethyl-4'-methanesulphonylbenzophenone
Formula (IV): A=phenyl, $Y_1$=4-$CF_3$, $Y_2$=H
Prepared by the procedure of Example 39.
Crystals melting at 138° C.

EXAMPLE 118
3-ethoxycarbonyl-4-(4-trifluoromethylphenyl)-4-(4-methanesulphonylphenyl)-3-butenoic acid
Formula (X): A=phenyl, $Y_1$=4-$CF_3$, $Y_2$=H
Prepared by the procedure of Example 11.
Oil used as such in the next step.

EXAMPLE 119
Ethyl 3-(4-trifluoromethylphenyl)-3-(4-methanesulphonylphenyl)-2-(2-hydroxyethyl)-2-propenoate
Formula (XI): A=phenyl, $Y_1$=4-$CF_3$, $Y_2$=H
Prepared by the procedure of Example 12.
Oil used as such in the next step.

EXAMPLE 120
(E)-3-[1-(4-trifluoromethylphenyl)-1-(4-methanesulphonylphenyl)methylidene]-dihydro-furan-2-one
(E) isomer:Formula (I): A=B=phenyl, $Y_1$=4-$CF_3$, $Y_2$=H, $X_1$=4-$SO_2CH_3$, $X_2$=H, $R_1R_2$=O, $R_3$=$R_4$=H
Prepared by the procedure of Example 65, purified by chromatography in a dichloromethane\acetone mixture (10/0.3).
Crystals melting at 188–189° C.

EXAMPLE 121
4-benzylthio-4'-chlorobenzophenxone
Prepared by the procedure of Example 56 from 4-bromochlorobenzene and 4-benzylthiobenzonitrile prepared in Example 55.
Crystals melting at 134° C.

EXAMPLE 122
4-t-butylaminosulphonyl-4'-chlorobenzophenone
Prepared by the procedure of Example 57.
Crystals melting at 163° C.

EXAMPLE 123
3-ethoxycarbonyl-4-(4-t-butylaminosulphonylphenyl) 4-(4-chlorophenyl)-3-butenoic acid
Formula (XII): A=phenyl, $Y_1$=4-Cl, $Y_2$=H
Prepared by the procedure of Example 58.
Oil used as such in the next step.

EXAMPLE 124
Ethyl (Z)-3-(4-t-butylaminosulphonylphenyl-3-(4-chlorophenyl)-2-(2-hydroxyethyl)-2-propenoate
Prepared by the procedure of Example 12. The oil obtained is taken up in diethyl ether and the crystals formed are filtered off (E isomer). The filtrate is concentrated under vacuum and the residue taken up in petroleum ether crystallises to give the (Z) isomer in the form of crystals melting at 120° C.

EXAMPLE 125
(Z)-4-[(4-chlorophenyl)-(2-oxo-dihydro-furan-3-ylidene)-methyl]benzenesulphonamide
Formula (I): A=B=phenyl, $Y_1$=4-Cl, $Y_2$=H, $X_1$=4-$SO_2NH_2$, $X_2$=H, $R_1R_2$=O, $R_3$=$R_4$=H
A solution of 10 g of ethyl (Z)-3-(4-t-butylaminosulphonylphenyl)-3-(4-chlorophenyl)-2-(2-hydroxyethyl)-2-propenoate prepared in Example 124, in 80 ml of trifluoroacetic acid is heated under reflux for 15 hours. After evaporation of the solvent under vacuum, the residue is taken up in dichloromethane. The organic phase is washed with water and then dried over magnesium sulphate and evaporated under vacuum to give an oil which crystallises in an acetone/diisopropyl ether mixture giving 3.9 g of (Z)-4-[(4-chlorophenyl)-(2-oxo-dihydro-furan-3-ylidene)-methyl]benzenesulphonamide in the form of crystals melting at 187–189° C.

EXAMPLE 126
4-benzylthio-3'-fluoro-4'-methylbenzophenone
Prepared by the procedure of Example 56 from 4-bromo-2-fluorotoluene.
Crystals melting at 122° C.

EXAMPLE 127
4-t-butylaminosulphonyl-3'-fluoro-4'-methylbenzophenone
Prepared by the procedure of Example 57.
Crystals melting at 132° C.

EXAMPLE 128
(Z)-3-ethoxycarbonyl-4-(4-t-butylaminosulphonylphenyl)-4-(3-fluoro-4-methylphenyl)-3-butenoic acid
Formula (XII): A=phenyl, $Y_1$=3-F, $Y_2$=4-$CH_3$
Prepared by the procedure of Example 58, the oil obtained being taken up in t-butyl-methyl ether and the crystals formed being filtered off giving the (E) isomer of melting point 96° C. The filtrate is concentrated under vacuum to give the (Z) isomer in the form of an oil used as such in the next step.

EXAMPLE 129
Ethyl (Z)-3-(4-t-butylaminosulphonylphenyl)-3-(3-fluoro-4-methylphenyl)-2-(2-hydroxyethyl)-2-propenoate Prepared by the procedure of Example 12 from the (Z) isomer of the acid of Example 128.

Oil used as such in the next step.

EXAMPLE 130
(Z)-4-[(3-fluoro-4-methylphenyl)-(2-oxo-dihydrofuran-3-ylidene)methyl]benzenesulphonamide Formula (I): A=B=phenyl, $Y_1$=3-F, $Y_2$=4-$CH_3$, $X_1$=4-$SO_2NH_2$, $X_2$=H, $R_1R_2$=O, $R_3$=$R_4$=H Prepared by the procedure of Example 125.

Crystals melting at 170–172° C.

EXAMPLE 131
4-benzylthio-4'-fluoro-3'-methylbenzophenone

Prepared by the procedure of Example 56 from 5-bromo-2-fluorotoluene.

Crystals melting at 123° C.

EXAMPLE 132
4-t-butylaminosulphonyl-4'-fluoro-3'-methylbenzophenone

Prepared by the procedure of Example 57.

Crystals melting at 108° C.

EXAMPLE 133
(Z)-3-ethoxycarbonyl-4-(4-t-butylaminosulphonylphenyl)-4-(4-fluoro-3-methylphenyl)-3-butenoic acid Formula (XII): A=phenyl, $Y_1$=3-$CH_3$, $Y_2$=4-F Prepared by the procedure of Example 58, the oil obtained being taken up in t-butyl-methyl ether and the crystals formed being removed ((E) isomer). The filtrate is evaporated under vacuum to give the (Z) isomer in the form of an oil used as such in the next step.

EXAMPLE 134
Ethyl (Z)-3-(4-t-butylaminosulphonylphenyl)-3-(4-fluoro-3-methylphenyl)-2-(2-hydroxyethyl)-2-propenoate Prepared by the procedure of Example 12.

Crystals melting at 128° C.

EXAMPLE 135
(Z)-4-[(4-fluoro-3-methylphenyl)-(2-oxo-dihydrofuran-3-ylidene)methyl]benzenesulphonamide Formula (I): A=B=phenyl, $Y_1$=3-$CH_3$, $Y_2$=4-F, $X_1$=4-$SO_2NH_2$, $X_2$=H, $R_1R_2$=O, $R_3$=$R_4$=H Prepared by the procedure of Example 125.

Crystals melting at 228–229° C.

EXAMPLE 136
Ethyl (E)-3-(4-t-butylaminosulphonylphenyl)-3-(3-fluoro-4-methylphenyl)-2-(2-hydroxyethyl)-3-propenoate Prepared by the procedure of Example 12, from the (E) isomer of the acid of Example 128.

Oil used as such in the next step.

EXAMPLE 137
(E)-3-(4-t-butylaminosulphonylphenyl)-3-(3-fluoro-4-methylphenyl)-2-(2-hydroxyethyl)-3-propenoic acid A solution of 16 g of ethyl (E-3-(4-t-butylaminosulphonylphenyl)-3-(3-fluoro-4-methylphenyl)-2-(2-hydroxyethyl)-3-propenoate, prepared in Example 136, in 50 ml of ethanol containing 3 g of sodium hydroxide and 5 ml of water, is heated under reflux for 2 hours. The mixture is concentrated under vacuum, taken up in water, washed with diethyl ether and the acidified with dilute hydrochloric acid and extracted with dichloromethane. The organic phase is dried over magnesium sulphate and then evaporated to dryness under vacuum to give a residue which crystallises in diisopropyl ether giving 7.6 g of (E)-3-(4-t-butylaminosulphonylphenyl)-3-(3-fluoro-4-methylphenyl)-2-(2-hydroxyethyl)-3-propenoic acid in the form of crystals melting at 160° C.

EXAMPLE 138
(E)-2-[1-(4-t-butylaminosulphonylphenyl)-1-(3-fluoro-4-methylphenyl)methylidene]butane-1,4-diol To a solution of 7.8 g of (E)-3-(4-t-butylaminosulphonylphenyl)-3-(3-fluoro-4-methylphenyl)-2-(2-hydroxyethyl)-3-propenoic acid prepared in Example 137, in 50 ml of anhydrous tetrahydrofuran, are added dropwise 5 ml of borane/dimethyl sulphide complex. The mixture is stirred for 6 hours at room temperature and then 10 ml of methanol are added dropwise. The mixture is concentrated under vacuum, taken up with an aqueous solution of potassium carbonate and extracted with diethyl ether. The organic phase is dried over magnesium sulphate and evaporated under vacuum to give 6.3 g of (E)-2-[1-(4t-butylaminosulphonylphenyl)-1-(3-fluoro-4-methylphenyl)methylidene]butane-1,4-diol in the form of crystals melting at 106° C.

EXAMPLE 139
(E)-4-[(3-fluoro-4-methylphenyl)-(tetrahydrofuran-3-ylidene) methyl]benzenesulphonamide Formula (I): A=B=phenyl, $X_1$=3-F, $X_2$=4-$CH_3$, $Y_1$=4-$SO_2NH_2$, $Y_2$=H, $R_1$=$R_2$=$R_3$=$R_4$=H A solution of 6.3 g of (E)-2-[1-(4-t-butylaminosulphonylphenyl)-1-(3-fluoro-4-methylphenyl)methylidene]butane-1,4-diol prepared in Example 138 in 75 ml of trifluoroacetic acid is heated for 10 hours under reflux. The solvent is concentrated under vacuum and the residue is taken up in a dilute solution of sodium hydroxide, washed with dichloromethane and then acidified with dilute hydrochloric acid and extracted with dichloromethane. The organic phases are combined and dried over magnesium sulphate and then evaporated under vacuum. The residue is crystallised in tert-butyl methyl ether to give 4 g of (E)-4-[(3-fluoro-4-methylphenyl)-(tetrahydro-furan-3-ylidene)methyl]benzenesulphonamide in the form of crystals melting at 174–176° C.

EXAMPLE 140
4-benzylthio-3'-chloro-4'-fluorobenzophenone

Prepared by the procedure of Example 56, from 4-bromo-2-chlorofluorobenzene.

Crystals melting at 102° C.

141
4-t-butylaminosulphonyl-3'-chloro-4'-fluorobenzophenone

Prepared by the procedure of Example 57.

Crystals melting at 108° C.

EXAMPLE 142
3-ethoxycarbonyl-4-(4-t-butylaminosulphonylphenyl)-4-(3-chloro-4-fluorophenyl)-3-butenoic acid Formula (XII): A=phenyl, $Y_1$=3-Cl, $Y_2$=4-F Prepared by the procedure of Example 58.

Oil used as such in the next step.

EXAMPLE 143
(Z)-4-[(3-chloro-4-fluorophenyl)-(2-oxo-dihydro-furan-3-ylidene)methyl]benzenesulphonamide Formula (I): A=B=phenyl, $Y_1$=3-Cl, $Y_2$=4-F, $X_1$=4-$SO_2NH_2$, $X_2$=H, $R_1R_2$=O, $R_3$=$R_4$=H To a solution of 17 g of 3-ethoxycarbonyl-4-(4-t-butylamino sulphonylphenyl)-4-(3-chloro-4-fluorophenyl)-3-butenoic acid prepared in Example 142 in 150 ml of tetrahydrofuran are added dropwise 7 ml of borane/dimethyl sulphide complex. The mixture is stirred for 6 hours at room temperature and then 30 ml of ethanol are added dropwise. After the addition of an aqueous solution of potassium carbonate, the mixture is extracted with dichloromethane. The organic phase is dried and evaporated under vacuum. The residue (13.8 g) is taken up in 30 ml of ethanol containing a solution of 3 g of sodium hydroxide in 10 ml of water and the mixture is heated at 70° C. for 3 hours. The solvents are evaporated off under vacuum and the residue is taken up in water; the aqueous phase is washed with diethyl ether, acidified with hydrochloric acid and extracted with dichloromethane, dried over magnesium sulphate and evaporated under vacuum. The residue is taken up in diethyl ether and the crystals obtained are filtered off giving 3 g of (E)-3-(4-t-butylaminosulphonylphenyl)-3-(3-fluoro-4-chlorophenyl)-2-(2-hydroxyethyl)-3-propenoic acid (melting point 180° C.). The filtrate is concentrated under vacuum and the residue is taken up in 60 ml of trifluoroacetic acid. The mixture is heated for 17 hours under reflux and then concentrated under vacuum. The residue is taken up with a diluted sodium hydroxide solution and extracted with dichloromethane. The organic phase is dried over magnesium sulphate and then evaporated under vacuum to give 2 g of (Z)-4-[(3-chloro-4-fluorophenyl)-(2-oxo-dihydro-furan-3-ylidene)methyl]benzene sulphonamide in the form of crystals melting at 244–246° C.

EXAMPLE 144

4-benzylthio-3'-fluoro-4'-methoxybenzophenone
Prepared by the procedure of Example 56 from 4-bromo-2-fluoroanisole.
Crystals melting at 125° C.

EXAMPLE 145

4-t-butylaminosulphonyl-3'-fluoro-4'-methoxybenzophenone
Prepared by the procedure of Example 57.
Crystals melting at 136° C.

EXAMPLE 146

(Z)-3-ethoxycarbonyl-4-(4-t-butylaminosulphonylphenyl)-4-(3-fluoro-4-methoxyphenyl)-3-butenoic acid
Formula (XII): A=phenyl, $Y_1$=3-F, $Y_2$=4-OMe
Prepared by the procedure of Example 58, the oil obtained is taken up in t-butyl methyl ether to give the (Z) isomer in the form of amorphous crystals used as such in the next step.

EXAMPLE 147

Ethyl (Z)-3-(4-t-butylaminosulphonylphenyl)-3-(3-fluoro-4-methoxyphenyl)-2-(2-hydroxyethyl)-2-propenoate
Prepared by the procedure of Example 12.
Oil used as such in the next step.

EXAMPLE 148

(Z)-4-[(3-fluoro-4-methoxyphenyl)-(2-oxo-dihydro-furan-3-ylidene)methyl]benzenesulphonamide
Formula (I): A=B=phenyl, $Y_1$=3-F, $Y_2$=4-OMe, $X_1$=4-$SO_2NH_2$, $X_2$=H, $R_1R_2$=O, $R_3$=$R_4$=H
Prepared by the procedure of Example 125.
Crystals melting at 149–150° C.

EXAMPLE 149

3-(4-fluorobenzoyl)pyridine
To a suspension of 140 g of nicotinic acid chloride hydrochloride in 500 ml of fluorobenzene cooled to 0° C. are added 280 g of aluminium chloride portionwise. The mixture is held under reflux for 6 hours, cooled and then poured onto ice. After the addition of sodium hydroxide up to pH=8, the mixture is extracted with dichloromethane. The organic phase is dried over magnesium sulphate and then evaporated under vacuum. The residue crystallises in a pentane/diisopropyl ether mixture giving 108.5 g of 3-(4-fluorobenzoyl)pyridine in the form of crystals melting at 91° C.

EXAMPLE 150

3-(4-benzylthiobenzoyl)pyridine
To a solution of 43 g of benzylmercaptan in 500 ml of N,N-dimethyl formamide are added 14 g of 60% sodium hydroxide. The mixture is stirred for 20 minutes at room temperature and 70 g of 3-(4-fluorobenzoyl)pyridine, prepared in Example 149, are added. The mixture is heated for 8 hours at 80° C., concentrated under vacuum and then the residue is taken up in water. The crystals formed are filtered off, dissolved in dichloromethane and the solution is dried over magnesium sulphate and concentrated under vacuum. The residue crystallises in a pentane/diisopropyl ether mixture to give 81 g of 3-(4-benzylthiobenzoyl)pyridine in the form of crystals melting at 102° C.

EXAMPLE 151

3-(4-t-butylaminosulphonylbenzoyl)pyridine
Prepared by the procedure of Example 57.
Crystals melting at 179° C.

EXAMPLE 152

(Z)-3-ethoxycarbonyl-4-(4-t-butylaminosulphonylphenyl)-4-(3-pyridyl)-3-butenoic acid
Formula (XII): A=3-pyridyl, $Y_1$=$Y_2$=H
Prepared by the procedure of Example 58, the oil obtained being taken up in hot ethyl acetate, the crystals formed being filtered off ((E) isomer of melting point 209° C.). The filtrate is evaporated and the residue taken up in pentane crystallises giving the (Z) isomer in the form of crystals melting at 195° C.

EXAMPLE 153

Ethyl (Z)-3-(4-t-butylaminosulphonylphenyl)-3-(3-pyridyl)-2-(2-hydroxyethyl)-2-propenoate
Prepared by the procedure of Example 12.
Amorphous crystals used as such in the next step.

EXAMPLE 154

(Z)-[(3-pyridyl)-(2-oxo-dihydro-furan-3-ylidene)methyl]benzenesulphonamide
Formula (I): A=3-pyridyl, B=phenyl, $X_1$=4-$SO_2NH_2$, $X_2$=H, $Y_1$=$Y_2$=H, $R_1R_2$=O, $R_3$=$R_4$=H
Prepared by the procedure of Example 125.
Crystals melting at 219–220° C.

EXAMPLE 155

3-chloro-4-methoxy-4'-methylthiobenzophenone
Formula (III): A=phenyl, $Y_1$=3-Cl, $Y_2$=4-OMe
Prepared by the procedure of Example 1.
Crystals melting at 100° C.

EXAMPLE 156

3-chloro-4-methoxy-4'-methanesulphonylbenzophenone
Formula (IV): A=phenyl, $Y_1$=3-Cl, $Y_2$=4-OMe
Prepared by the procedure of Example 39.
Crystals melting at 164° C.

EXAMPLE 157

(Z)-3-ethoxycarbonyl-4-(3-chloro-4-methoxyphenyl)-4-(4-methanesulphonylphenyl)-3-butenoic acid Formula (X): A=phenyl, $Y_1$=3-Cl, $Y_2$=4-OMe Prepared by the procedure of Example 11, the oil obtained being taken up in ether and the crystals formed being filtered off to give the (Z) isomer in the form of crystals melting at 179° C.

EXAMPLE 158

Ethyl (Z)-3-(3-chloro-4-methoxyphenyl)-3-(4-methanesulphonylphenyl)-2-(2-hydroxyethyl)-3-propenoate Formula (XI): A=phenyl, $Y_1$=3-Cl, $Y_2$=4-OMe Prepared by the procedure of Example 12.
Crystals melting at 102° C.

EXAMPLE 159

(Z)-3-[1-(3-chloro-4-methoxyphenyl)-1-(4-methanesulphonyl phenyl)methylidene]-dihydro-furan-2-one Formula (I): A=B=phenyl, $Y_1$=3-Cl, $Y_2$=4-OMe, $X_1$=4-$SO_2CH_3$, $X_2$=H, $R_1R_2$=O, $R_3$=$R_4$=H Prepared by the procedure of Example 65.
Crystals melting at 177° C.

EXAMPLE 160

2-(4-methylthiobenzoyl)thiophene

Formula (III): A=2-thienyl, $Y_1$=$Y_2$=H

Prepared by the procedure of Example 1.
Crystals melting at 60° C.

EXAMPLE 161

2-(4-methanesulphonylbenzoyl)thiophene

Formula (IV): A=2-thienyl, $Y_1$=$Y_2$=H

Prepared by the procedure of Example 39.
Crystals melting at 140° C.

EXAMPLE 162

(E)-3-ethoxycarbonyl-4-(4-methanesulphonylphenyl)-4-(2-thienyl)-3-butenoic acid

Formula (X): A=2-thienyl, $Y_1$=$Y_2$=H

Prepared by the procedure of Example 11.
Crystals melting at 120° C.

EXAMPLE 163

Ethyl (E)-3-(4-methanesulphonylphenyl)-3-(2-thienyl)-2-(2-hydroxyethyl)-2-propenoate Formula (XI): A=2-thienyl, $Y_1$=$Y_2$=H Prepared by the procedure of Example 12.
Crystals melting at 116° C.

EXAMPLE 164

(E)-3-[1-(4-methanesulphonylphenyl)-1-(2-thienyl)methylidene]dihydrofuran-2-one

Formula (I): A=2-thienyl, B=phenyl, $Y_1$=$Y_2$=H, $X_1$=4-$SO_2CH_3$, $X_2$=H, $R_1R_2$=O, $R_3$=$R_4$=H Prepared by the procedure of Example 65.
Crystals melting at 246° C.

EXAMPLE 165

4-(2-naphthoyl)methylthiobenzene

Formula (III): A=2-naphthyl, $Y_1$=$Y_2$=H

Prepared by the procedure of Example 1.
Crystals melting at 98° C.

EXAMPLE 166

4(2-napthyl)methanesulfonylbenzene

Formula (IV): A=2-napthyl, $Y_1$=$Y_2$=H

Prepared by the procedure of Example 39.
Crystals meting at 150 ° C.

EXAMPLE 167

3-Ethoxycarbonyl-4-(2-napthyl)-4-(4-methanesulphonyl phenyl)-3-butenoic acid

Formula (X): A=2-napthyl, $Y_1$=$Y_2$=H

Prepared by the procedure of Example 39.
Oil used as such in the next step.

EXAMPLE 168

Ethyl 3-(2-napthyl)-3-(4-methanesulphonylphenyl)-2-(2-hydroxyethyl)-2-propenoate Formula (XI): A=2-napthyl, $Y_1$=$Y_2$=H Prepared by the procedure of Example 12.
Oil used as such in the next step.

EXAMPLE 169

(Z)-3-[1-(2-napthyl)-1-(4-methanesulfonylphenyl)methyliden]-dihydro-furan-2-one

Formula (I): A=2-napthyl, B=phenyl, $Y_1$=$Y_2$=H $X_1$=4-$SO_2CH_3$, $X_2$=H, $R_1R_2$=O, $R_3$=$R_4$=H Prepared by the procedure of Example 65, purified by chromatography in dichioromethane/acetone mixture (10/0.3)

Crystals melting at 244° C.

The following 4-benzylthiobenzophenones were prepared according to the procedure of example 56 proceeding from the appropriate bromobenzene derivatives.

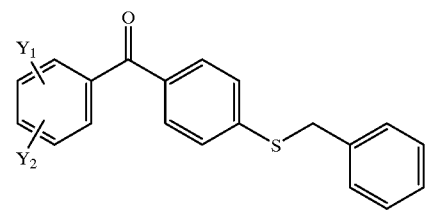

| Example | $Y_1$ | $Y_2$ | mp(° C.) |
|---|---|---|---|
| 170 | 3-Cl | 5-Cl | 80 |
| 171 | 3-$CH_3$ | H | 98 |
| 172 | 3-Cl | H | 90 |
| 173 | 3-Cl | 4-Cl | 90 |
| 174 | 4-$CH_3$ | H | 108 |
| 175 | 3-F | 4-Cl | 110 |
| 176 | 3-F | H | 85 |
| 177 | 4-$CF_3$ | H | 140 |
| 178 | 3-$CF_3$ | H | 68 |
| 179 | 3-$OCH_3$ | H | amorphous |
| 180 | 3-F | 4-F | 86 |
| 181 | 3-Cl | 4-$CH_3$ | oil |
| 182 | 3-$CH_3$ | 4-$OCH_3$ | amorphous |
| 183 | 4-$OCH_3$ | H | 117° C. |

The following 4-(t-butylaminosulfonyl)benzophenones were prepared according to example 57:

| Example | $Y_1$ | $Y_2$ | mp(° C.) |
|---|---|---|---|
| 184 | 3-Cl | 5-Cl | 144 |
| 185 | 3-CH$_3$ | H | 120 |
| 186 | 3-Cl | H | 128 |
| 187 | 3-Cl | 4-Cl | 130 |
| 188 | 4-CH$_3$ | H | 132 |
| 189 | 3-F | 4-Cl | 100 |
| 190 | 3-F | H | 96 |
| 191 | 4-CF$_3$ | H | 114 |
| 192 | 3-CF$_3$ | H | 110 |
| 193 | 3-OCH$_3$ | H | oil |
| 194 | 3-F | 4-F | 115 |
| 195 | 3-Cl | 4-CH$_3$ | 105 |
| 196 | 3-CH$_3$ | 4-OCH$_3$ | 127 |
| 197 | 4-OCH$_3$ | H | 134 |

The following acid-esters of formula (XII) were prepared according to example 58:

| Example | $Y_1$ | $Y_2$ | mp(° C.) |
|---|---|---|---|
| 198 | 3-Cl | 5-Cl | oil |
| 199 | 3-CH$_3$ | H | 134 |
| 200 | 3-Cl | H | oil |
| 201 | 3-Cl | 4-Cl | 118 |
| 202 | 4-CH$_3$ | H | oil |
| 203 | 3-F | 4-Cl | oil |
| 204 | 3-F | H | 148 |
| 205 | 4-CF$_3$ | H | oil |
| 206 | 3-CF$_3$ | H | oil |
| 207 | 3-OCH$_3$ | H | oil |
| 208 | 3-F | 4-F | oil |
| 209 | 3-Cl | 4-CH$_3$ | oil |
| 210 | 3-CH$_3$ | 4-OCH$_3$ | oil |
| 211 | 4-OCH$_3$ | H | oil |

The following alcohol-esters were prepared according to example 59:

| Example | $Y_1$ | $Y_2$ | mp(° C.) |
|---|---|---|---|
| 212 | 3-Cl | 5-Cl | oil |
| 213 | 3-CH$_3$ | H | 127 |
| 214 | 3-Cl | H | oil |
| 215 | 3-Cl | 4-Cl | oil |
| 216 | 4-CH$_3$ | H | 112 |
| 217 | 3-F | 4-Cl | 118 |
| 218 | 3-F | H | 128 |
| 219 | 4-CF$_3$ | H | 118 |
| 220 | 3-CF$_3$ | H | oil |
| 221 | 3-OCH$_3$ | H | oil |
| 222 | 3-F | 4-F | 132 |
| 223 | 3-Cl | 4-CH$_3$ | oil |
| 224 | 3-CH$_3$ | 4-OCH$_3$ | oil |
| 225 | 4-OCH$_3$ | H | oil |

The following sulfonamide compounds of formula (I) were prepared according to example 60:

Formula (I):
A = B = phenyl, $X_1$ = 4-SO$_2$NH$_2$,
$X_2$ = H, $R_1R_2$ = O, $R_3$ = $R_4$ = H

| Example | $Y_1$ | $Y_2$ | mp(° C.) |
|---|---|---|---|
| 226 | 3-Cl | 5-Cl | 217 |
| 227 | 3-CH$_3$ | H | 176 |
| 228 | 3-Cl | H | 182 |
| 229 | 3-Cl | 4-Cl | 210 |
| 230 | 4-CH$_3$ | H | 189 |
| 231 | 3-F | 4-Cl | 197 |
| 232 | 3-F | H | 192 |
| 233 | 4-CF$_3$ | H | 155 |
| 234 | 3-CF$_3$ | H | 111 |
| 235 | 3-OCH$_3$ | H | 152 |
| 236 | 3-F | 4-F | 194 |
| 237 | 3-Cl | 4-CH$_3$ | 184 |

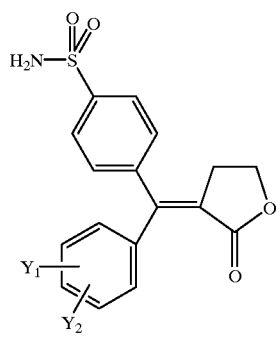

Formula (I):
A = B = phenyl, $X_1$ = 4-$SO_2NH_2$,
$X_2$ = H, $R_1R_2$ = O, $R_3$ = $R_4$ = H

| Example | $Y_1$ | $Y_2$ | mp(° C.) |
|---|---|---|---|
| 238 | 3-$CH_3$ | 4-$OCH_3$ | 211 |
| 239 | 4-$OCH_3$ | H | 154 |

EXAMPLE 240
4-benzylthio-3-fluorobenzonitrile

To a solution of 25 g of 3,4-difluorobenzonitrile in 100 ml of N,N-dimethylformamide is added 25 g of potassium carbonate and 22.3 g of benzylmercaptan. The mixture is stirred for 3 hours at room temperature and water is added. The crystals are filtered off, washed with water and pentane and dried to give 41 g of 4-benzylthio-3-fluorobenzonitrile in the form of crystals melting at 87° C.

EXAMPLE 241
4-benzylthio-3-fluoro-4'-chlorobenzophenone

Prepared according to the procedure of example 56 from 4-bromochloro benzene and 4-benzylthio-3-fluorobenzonitrile prepared in example 240.

Crystals melting at 120° C.

The following 4-benzylthio-3-fluorobenzophenones were prepared according to the procedure of example 241 proceeding from the appropriate bromobenzene derivative.

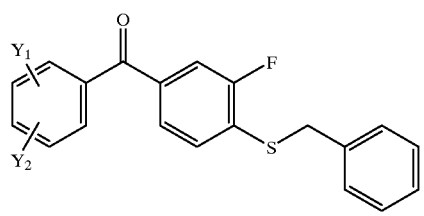

| Example | $Y_1$ | $Y_2$ | mp(° C.) |
|---|---|---|---|
| 242 | 4-F | H | 87 |
| 243 | 4-$CH_3$ | H | 102 |
| 244 | 3-$CH_3$ | H | oil |
| 245 | 3-F | 4-$CH_3$ | 125 |
| 246 | 3-Cl | 4-$CH_3$ | 104 |
| 247 | 3-Cl | 4-F | 110 |
| 248 | 3-$CH_3$ | 4-$OCH_3$ | 100 |

EXAMPLE 249
4-t-Butylaminosulfonyl-3-fluoro-4'-chlorobenzophenone

Chlorine (40 g) is bubbled up into a solution of 53 g of 4-benzylthio-3-fluoro-4'-chlorobenzophenone, prepared in example 241 in 300 ml of acetic acid and 6 ml of water. The mixture is then stirred for 5 hours at room temperature, water is added and the crystals are filtered off, washed with water then with di-isopropyl ether to give 37 g of sulfonyl chloride. To this sulfonyl chloride in 200 ml of dichloromethane is added dropwise a solution of 35 ml of t-butylamine in 100 ml of dichloromethane. The mixture is stirred for 4 hours at room temperature, washed with a dilute solution of hydrochloric acid and the organic layer is dried over magnesium sulfate then concentrated under vacuum to give 38.5 g of 4-t-Butylaminosulfonyl-3-fluoro-4'-chlorobenzophenone, melting at 152° C.

The following 4-t-butylaminosulfonyl-3-fluorobenzophenones were prepared according to the procedure of example 249.

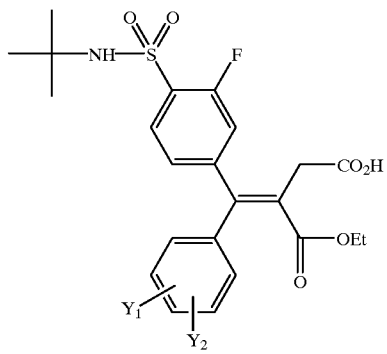

| Example | $Y_1$ | $Y_2$ | mp(° C.) |
|---|---|---|---|
| 250 | 4-F | H | 132 |
| 251 | 4-$CH_3$ | H | 130 |
| 252 | 3-$CH_3$ | H | 133 |
| 253 | 3-F | 4-$CH_3$ | 132 |
| 254 | 3-Cl | 4-$CH_3$ | 152 |
| 255 | 3-Cl | 4-F | 128 |
| 256 | 3-$CH_3$ | 4-$OCH_3$ | 156 |

The following acid-esters were prepared according to the procedure of example 58 proceeding form the appropriate 4-t-butylaminosulfonyl-3-fluorobenzophenones.

| Example | $Y_1$ | $Y_2$ | mp(° C.) |
|---|---|---|---|
| 257 | 4-Cl | H | 100 |
| 258 | 4-F | H | 160 |
| 259 | 4-$CH_3$ | H | 156 |
| 260 | 3-$CH_3$ | H | oil |
| 261 | 3-F | 4-$CH_3$ | oil |
| 262 | 3-Cl | 4-$CH_3$ | oil |
| 263 | 3-Cl | 4-F | oil |
| 264 | 3-$CH_3$ | 4-$OCH_3$ | oil |

The following alcohol-esters were prepared according to the procedure example 59 proceeding from the appropriate acid-esters.

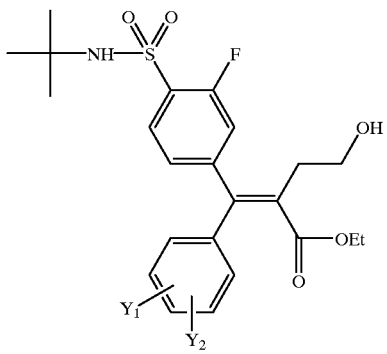

| Example | Y$_1$ | Y$_2$ | mp(° C.) |
|---|---|---|---|
| 265 | 4-Cl | H | 130 |
| 266 | 4-F | H | 102 |
| 267 | 4-CH$_3$ | H | oil |
| 268 | 3-CH$_3$ | H | 156 |
| 269 | 3-F | 4-CH$_3$ | 104 |
| 270 | 3-Cl | 4-CH$_3$ | oil |
| 271 | 3-Cl | 4-F | 138 |
| 272 | 3-CH$_3$ | 4-OCH$_3$ | 128 |

The following sulfonamide compounds of formula (I) were prepared according to the procedure of example 60.

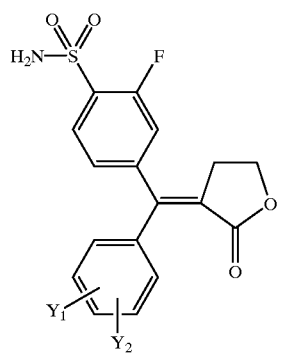

Formula (I):
A = B = phenyl, X$_1$ = 4-SO$_2$NH$_2$,
X$_2$ = 3-F, R$_1$R$_2$ = O, R$_3$ = R$_4$ = H

| Example | Y$_1$ | Y$_2$ | mp(° C.) |
|---|---|---|---|
| 273 | 4-Cl | H | 187 |
| 274 | 4-F | H | 165 |
| 275 | 4-CH$_3$ | H | 225 |
| 276 | 3-CH$_3$ | H | 140 |
| 277 | 3-F | 4-CH$_3$ | 169 |
| 278 | 3-Cl | 4-CH$_3$ | 180 |
| 279 | 3-Cl | 4-F | 224 |
| 280 | 3-CH$_3$ | 4-OCH$_3$ | 191 |

PHARMACOLOGY

The anti-inflarnmatory activity of the compounds of the Examples was evaluated by the carrageenin oedema method and the analgesic activity was evaluated by the kaolin arthritis method.

Methods
Anti-inflammatory Activity:
The anti-inflammatory activity is evaluated in the rat by the carrageenin oedema test. The product is administered orally at a rate of 2.5 ml/100 g (n=6 animals per dose) 2 h 30 min after oral hyperhydration (2.5 m/100 g); one hour after administration of the product, the oedema is induced by the plantar subcutaneous injection of 2% aqueous carrageenin solution. The results are expressed as the ID$_{50}$, the dose in mg/kg which induces 50% decrease in the volume of the oedema, calculated by linear regression using the maximum oedema volume obtained for each product tested.

Analgesic activity:
The analgesic activity is evaluated in the rat by the kaolin arthritis test. Thirty minutes after the intra-articular administration of 10% aqueous kaolin suspension, the product is administered orally at a rate of 1 ml/100 g (n=10 animals per dose). The results are expressed as DE$_{50}$, the dose in mg/kg which induces 50% decrease of the maximum quotation in the control batch, calculated by linear regression.

| Example | Anti-inflammatory activity ID$_{50}$ (mg/kg) | Analgesic activity DE$_{50}$ (mg/kg) |
|---|---|---|
| 4 (E isomer) | 1.8 | 7.6 |
| 8 (E isomer) | >30 | — |
| 8 and 65 (Z isomer) | 3.7 | 2.1 |
| 13 (Z isomer) | 3.9 | 14.1 |
| 18 (Z isomer) | >30 | 6.1 |
| 23 (Z isomer) | 9.3 | 7.2 |
| 28 (E isomer) | 10.1 | 26.1 |
| 31 (E isomer) | 3.1 | 14.2 |
| 34 (E isomer) | — | 38.8 |
| 49 (Z isomer) | >30 | >30 |
| 54 (Z isomer) | >30 | 10.8 |
| 60 (E isomer) | 1.7 | 20.9 |
| 70 (Z isomer) | 5.5 | 21.5 |
| 75 (Z isomer) | 4.6 | — |
| 80 (Z isomer) | 4.8 | 5.8 |
| 85 (E isomer) | >30 | >30 |
| 90 (Z isomer) | 17.2 | — |
| 95 (Z isomer) | 1.6 | 5.8 |
| 100 (Z isomer) | 3.6 | — |
| 125 (Z isomer) | 1.8 | 8.5 |
| 130 (Z isomer) | 2.0 | 2.4 |
| 135 (Z isomer) | 3.3 | 6.1 |
| 143 (Z isomer) | 0.7 | 6.4 |

Chemoprevention Assays in Mice:
The test molecule is given in the feed to apc/min mice, a mouse model of human familial adenomatous polyposis, at 1.8 mg/kg/day for 240 days. The viability and the average tumor burden in animals receiving the test compound is compared to that in control animals.

Results:
Mice that received 1.8 mg/kg/day of the compound of example 65 in the feed were outliving their control counterparts after 240 days. In the treated group, 17/29 were still alive and have an average tumor burden of 11.9 tumors per mouse. In the control group, animals not receiving the test compound, only 8/29 mice were still alive with an average tumor burden of 16.3 tumors in the specific areas of the gastrointestinal tract observed.

Inhibition of the COX-1 and COX-2 Enzymatic Activities
The test molecule is preincubated for 10 minutes at 25° C. with 2 U of COX-1 (purified enzyme from ram seminal vesicles) or 1 U of COX-2 (purified enzyme from ewe placenta). Arachidonic acid (6 $\mu$M for COX-1, 4 $\mu$M for COX-2) is added to the reaction medium and incubation is carried out for 5 minutes at 25° C. When incubation has ended, the enzymatic reaction is stopped by the addition of 1 N HCl and the PGE2 produced is determined by EIA.

The results are expressed as $IC_{50}$, the concentration in nM which corresponds to 50% inhibition of the maximal enzymatic activity on the COX-1 and COX-2 (n=1 to 4 determinations).

| Example | COX-2 Inhibition $IC_{50}$ (nM) | COX-1 Inhibition $IC_{50}$ (nM) | Selectivity COX-1/COX-2 ratio |
|---|---|---|---|
| 4 (E) | 674 ± 46 (n = 3) | >300,000 | >445 |
| 8 or 65 (Z) | 182 ± 25 (n = 4) | 171875 ± 22193 (n = 4) | 944 |
| 13 (Z) | 610 | >100,000 | >164 |
| 18 (Z) | 132 ± 32 (n = 2) | 73200 | 555 |
| 23 (E) | 627 | >100,000 | >159 |
| 28 (E) | 18354 | >10,000 | >0.5 |
| 31 (E) | 780 | >100,000 | >128 |
| 34 (E) | 694 | >100,000 | >144 |
| 49 (Z) | 418 | >100,000 | >239 |
| 54 (Z) | 710 | >100,000 | >141 |
| 60 (E) | 296 ± 107 (n = 2) | 81000 | 274 |
| 70 (Z) | 225 | >100,000 | >444 |
| 80 (Z) | 518 | >100,000 | >193 |
| 85 (E) | 350 | >100,000 | >286 |
| 90 (Z) | 458 | >100,000 | >218 |
| 95 (Z) | 205 ± 35 (n = 2) | 309500 ± 27500 (n = 2) | 1510 |
| 100 (Z) | 166 | 62000 | 373 |
| 125 (Z) | 60 | 2525 ± 1312 (n = 2) | 42 |
| 130 (Z) | 131 ± 19 (n = 2) | 45730 | 349 |
| 135 (Z) | 245 ± 76 (n = 2) | 19700 | 80 |
| 143 (Z) | 73 | 12700 | 174 |

TOLERANCE

Gastric Tolerance:

The gastric tolerance is studied on Charles River rats of the CD strain weighing between 110 and 150 g. The animals are placed on a water diet 24 h prior to oral administration of the product or the vehicle only at a rate of 1 ml/100 g (n=6 animals per dose). Six hours after administration, the animals are sacrificed and the stomachs are removed and opened along the large curvature. The number of haemorrhagic puncta and sulci per stomach, identified macroscopically, makes it possible to establish an ulceration index (0: no lesion, 1: 1 to 2 lesions, 2: 3 to 4 lesions, 3: 5 to 8 lesions, 4: 9 to 16 lesions, 5: more than 17 lesions) and to estimate the 50% ulcerigenic dose ($UD_{50}$=dose inducing 4 to 5 lesions, expressed in mg/kg).

| Example | $UD_{50}$ (confidence limit) mg/kg |
|---|---|
| 4 (E isomer) | >1000 |
| 8 or 65 (Z isomer) | >1000 |
| 125 (Z isomer) | >1000 |
| indomethacin | 8.3 (5.8–11.8) |

TOXICOLOGY

The first toxicology studies performed show that the products of the Examples do not induce a deleterious effect in the rat after the oral absorption of doses ranging up to 300 mg/kg.

What is claimed is:

1. A diarylmethylidenefuran compound of formula (I):

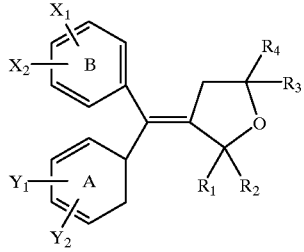

Formula (I)

wherein:
the rings A and B independently are:
a phenyl radical:
a napthyl radical;
a pyridyl radical;
at least one of said rings A and B necessarily representing a phenyl radical;
at least one of the substituents $X_1$, $X_2$, $Y_1$ or $Y_2$ is necessarily:
an $S(O)_n$—R group, in which n is an integer equal to 0, 1 or 2 and R is a lower alkyl radical having 1 to 6 carbon atoms or a lower haloalkyl radical having 1 to 6 carbon atoms, or
an $SO_2NH_2$ group;
and is located in the para position on said phenyl radical when A or B represents a phenyl radical,
the others independently being:
a hydrogen atom,
a halogen atom,
a lower alkyl radical having 1 to 6 carbon atoms,
a trifluoromethyl radical,
a lower O-alkyl radical having 1 to 6 carbon atoms, or
$X_1$ and $X_2$ or $Y_1$ and $Y_2$ are a methylenedioxy group; and
$R_1$, $R_2$, $R_3$ and $R_4$ independently are:
a hydrogen atom,
a halogen atom,
a lower alkyl radical having 1 to 6 carbon atoms,
a lower haloalkyl radical having 1 to 6 carbon atoms,
an aromatic radical selected from the group consisting of phenyl and naphthyl; or
$R_1R_2$ or $R_3R_4$ are an oxygen atom, or
$R_1R_2$ or $R_3R_4$, together with the carbon atom to which they are attached, form a saturated hydrocarbon ring having from 3 to 7 carbon atoms.

2. A compound of formula (I) according to claim 1, wherein:
the rings A and B independently are:
a phenyl radical,
a naphthyl radical,
a pyridyl radical;
at least one of the substituents $X_1$, $X_2$, $Y_1$ or $Y_2$ is necessarily and $SCH_3$, $SO_2CH_3$ or $SO_2NH_2$ group,
the others independently being:
a hydrogen atom,
a halogen atom,
a lower alkyl radical having 1 to 6 carbon atoms,
a trifluoromethyl radical, or
a lower O-alkyl radical having 1 to 6 carbon atoms;
$R_1R_2$ are an oxygen atom; and
$R_3R_4$ independently are a hydrogen atom or a lower alkyl radical having 1 to 6 carbons.

3. A compound according to claim 1, wherein the ring B is a phenyl radical.

4. A compound according to claim 1, wherein the ring A is a phenyl radical or a pyridyl radical.

5. A compound according to claim 1, wherein $X_1$ is a 4-$SO_2CH_3$ group or a 4-$SO_2NH_2$ group, and $X_2$ is a hydrogen atom.

6. A compound according to claim 1, wherein $Y_1$ is a fluorine atom, a chlorine atom, a bromine atom or a methyl radical, and $Y_2$ is a hydrogen atom, a fluorine atom, a chlorine atom, or a bromine atom.

7. A compound according to claim 1, wherein $R_1R_2$ are an oxygen atom and $R_3$ and $R_4$ are each a hydrogen atom.

8. A compound according to claim 1, and having the formula

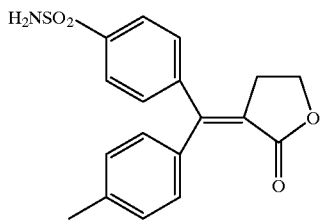

9. A compound according to claim 1 which is (E)-4-[(4-methylphenyl)(tetrahydro-2-oxo-3-furanylidene)methyl] benzenesulfonamide or (Z)-3-[1-(4-bromophenyl)-1-(4-methylsulfonylphenyl)methylidene]dihydrofuran-2-one.

10. A compound according to claim 1 which is (Z)-3-[1-(4-bromophenyl)-1-(4-methylsulfonylphenyl)methylidene] dihydrofuran-2-one.

11. A pharmaceutical composition, which comprises a pharmaceutically effective amount of a compound of formula (I) as defined in claim 1, incorporated in a pharmaceutically acceptable excipient, vehicle or carrier.

12. A pharmaceutical composition with anti-inflammatory and analgesic activity, which contains a pharmaceutically effective amount of a compound of formula (I) as defined claim 1, incorporated in a pharmaceutically acceptable excipient, vehicle or carrier.

13. A pharmceutical composition as defined in claim 1, useful in the prevention of cancer, in particular adenocarcinoma of the colon, in the prevention of neurodegenerative diseases, especially Alzheimer's disease, in the prevention of stroke and epilepsy, and in the prevention of premature labour.

14. A pharmaceutical composition according to claim 11, which is in the form of gelatin capsules or tablets containing a dose of 1 mg to 1000 mg.

15. A pharmaceutical composition according to claim 11, which is in the form of of injectable preparations containing a dose of 0.1 mg to 500 mg.

16. A method for treating inflammation in a mammal which comprises adminstering an anti-inflammatory effective amount of a compound of formula I as defined in claim 1 to said mammal.

17. A method for treating pain in a mammal which comprises administering an effective amount of a compound of formula I as defined in claim 1 to said mammal.

* * * * *